US008790870B2

(12) United States Patent
Stuyver et al.

(10) Patent No.: US 8,790,870 B2
(45) Date of Patent: Jul. 29, 2014

(54) QUANTITATIVE HIV PHENOTYPE OR TROPISM ASSAY

(75) Inventors: Lieven Jozef Stuyver, Herzele (BE); Kurt Van Baelen, Geel (BE); Ina Isabel Vandenbroucke, Verrebroek (BE)

(73) Assignee: Virco BVBA, Mechelen (BE)

( * ) Notice: Subject to any disclaimer, the term of this patent is extended or adjusted under 35 U.S.C. 154(b) by 661 days.

(21) Appl. No.: 12/159,813

(22) PCT Filed: Feb. 2, 2007

(86) PCT No.: PCT/EP2007/051035
§ 371 (c)(1),
(2), (4) Date: Jul. 1, 2008

(87) PCT Pub. No.: WO2007/088201
PCT Pub. Date: Aug. 9, 2007

(65) Prior Publication Data
US 2009/0047661 A1 Feb. 19, 2009

(30) Foreign Application Priority Data

Feb. 3, 2006 (EP) ..................................... 06101294
Jun. 13, 2006 (EP) ..................................... 06115363

(51) Int. Cl.
*C12Q 1/70* (2006.01)
*C12N 15/00* (2006.01)

(52) U.S. Cl.
USPC ........................................... 435/5; 435/320.1

(58) Field of Classification Search
None
See application file for complete search history.

(56) References Cited

U.S. PATENT DOCUMENTS

| | | | |
|---|---|---|---|
| 6,057,102 A | 5/2000 | Landau et al. | |
| 6,214,450 B1 | 4/2001 | Wickert et al. | |
| 6,727,060 B2 * | 4/2004 | Philpott et al. | 435/5 |
| 7,494,768 B1 * | 2/2009 | Hertogs et al. | 435/5 |
| 2002/0182592 A1 | 12/2002 | Petropoulos et al. | |
| 2003/0124514 A1 | 7/2003 | Vingerhoets et al. | |
| 2004/0073378 A1 | 4/2004 | Dehertogh et al. | |
| 2004/0110125 A1 | 6/2004 | Petropoulos et al. | |
| 2005/0233312 A1 | 10/2005 | De Meyer et al. | |

FOREIGN PATENT DOCUMENTS

| | | |
|---|---|---|
| DE | 10113042 B4 | 9/2002 |
| EP | 1185712 B1 | 3/2002 |
| WO | WO 01/27330 | 4/2001 |
| WO | WO 0157245 A2 | 8/2001 |
| WO | WO 0179540 A2 | 10/2001 |
| WO | WO 2004/003817 | 1/2004 |
| WO | WO 2004111907 A2 | 12/2004 |
| WO | WO 2005086061 A2 | 9/2005 |

OTHER PUBLICATIONS

Chesebro et al. Macrophage-tropic human immunodeficiency virus isolates from different pateints exhibit unusal V3 envelope sequence homogeneity in comparison with T-cell-tropic isolates. Journal of Virology 1992, vol. 66, No. 11, pp. 6547-6554.*
Chen, Benjamin K. et al., "The kB Sites in the Human Immunodeficiency Virus Type 1 Long Terminal Repeat Enhance Virus Replication yet Are Not Absolutely Required for Viral Growth", Journal of Virology, Jul. 1997, pp. 5495-5504, vol. 71, No. 7.
Deng, Hongkui et al., "Identification of a major co-receptor for primary isolates of HIV-1", Nature, Jun. 20, 1996, pp. 661-666, vol. 381.
Feng, Yu et al., "HIV-1 Entry Cofactor: Functional cDNA Cloning of a Seven-Transmembrane, G Protein-Coupled Receptor", Science, May 10, 1996, pp. 872-877, vol. 272.
Hoffman, Noah G. et al., "Variability in the Human Immunodeficiency Virus Type 1 gp 120 Env Protein Linked to Phenotype-Associated Changes in the V3 Loop", Journal of Virology, Apr. 2002, pp. 3852-3864, vol. 76, No. 8.
Hsu, Philip, "Mechanism of HIV-1 Acquired Resistance to Protease Inhibitors and Its Possible Limitations", Vaccine Revolution Human Biology 115B—Instructor: Robert Siegel, Mar. 20, 1997, pp. 1-5.
Jensen, Mark A. et al., "Improved Coreceptor Usage Prediction and Genotypic Monitoring of R5-toX4 Transition by Motif Analysis of Human Immunodeficiency Virus Type 1 *env* V3 Loop Sequences", Journal of Virology, Dec. 2003, pp. 13376-13388, vol. 77, No. 24.
Karlsson, Ingrid et al., "HIV biological variability unveiled: frequent isolations and chimeric receptors reveal unprecedented variation of coreceptor use", AIDS, 2003, pp. 2561-2569, vol. 17.
Kim, Frances M. et al., "V3-Independent Determinants of Macrophage Tropism in a Primary Human Immunodeficiency Virus Type 1 Isolate", Journal of Virology, Mar. 1995, pp. 1755-1761, vol. 69, No. 3.
Li, Ming et al., "Genetic and Neutralization Properties of Subtype C Human Immunodeficiency Virus Type 1 Molecular *env* Clones from Acute and Early Heterosexually Acquired Infections in Southern Africa", Journal of Virology, Dec. 2006, pp. 11776-11790, vol. 80, No. 23.
Trkola, Alexandra et al., "CD4-dependent, antibody-sensitive interactions between HIV-1 and its co-receptor CCR-5", Nature, Nov. 14, 1996, pp. 184-187, vol. 384.
"Chemokine (C-X-C motif) receptor 4," *Weizmann Institute of Science*; http://www.genecards.org/cgi-bin/carddisp.pl?gene=CXCR4; update Mar. 11, 2006; 12 pages.
"Chemokine (C-C motif) receptor 5," *Weizmann Institute of Science*; http://www.genecards.org/cgi-bin/carddisp.pl?gene=CCR5; update Mar. 11, 2006; 11 pages.
Siegal, "Vaccine Revolution", http://www.stanford.edu/siegelr/philhsu.htrn, Mar. 3, 1997, 2 pages.

* cited by examiner

*Primary Examiner* — Louise Humphrey
(74) *Attorney, Agent, or Firm* — Baker & Hosteler LLP

(57) ABSTRACT

The present invention concerns a method for predicting quantitative phenotype, e.g. gag-phenotype, integrase phenotype or tropism in a patient infected by Human Immunodeficiency Virus (HIV).

11 Claims, 6 Drawing Sheets

Figure 6

SEQUENCE LISTING

```
<160> NUMBER OF SEQ ID NOS: 6

<210> SEQ ID NO 1
<211> LENGTH: 25
<212> TYPE: DNA
<213> ORGANISM: Human immunodeficiency virus type 1

<400> SEQUENCE: 1
cagaagacag tggcaatgag agtga                                   25

<210> SEQ ID NO 2
<211> LENGTH: 21
<212> TYPE: DNA
<213> ORGANISM: Human immunodeficiency virus type 1

<400> SEQUENCE: 2
atgggagggg catacattgc t                                       21

<210> SEQ ID NO 3
<211> LENGTH: 20
<212> TYPE: DNA
<213> ORGANISM: Human immunodeficiency virus type 1

<400> SEQUENCE: 3
attaaccctc actaaaggga                                         20

<210> SEQ ID NO 4
<211> LENGTH: 20
<212> TYPE: DNA
<213> ORGANISM: Human immunodeficiency virus type 1

<400> SEQUENCE: 4
taatacgact cactataggg                                         20

<210> SEQ ID NO 5
<211> LENGTH: 15524
<212> TYPE: DNA
<213> ORGANISM: Human immunodeficiency virus type 1

<400> SEQUENCE: 5
gaatgcaatt gttgttgtta acttgtttat tgcagcttat aatggttaca aataaagcaa    60
tagcatcaca aatttcacaa ataaagcatt tttttcactg cattctagtt gtggtttgtc   120
```

```
caaactcatc aatgtatctt atcatgtctg gatcaactgg ataactcaag ctaaccaaaa      180
tcatcccaaa cttcccaccc catacccact taccactgcc aattacctgt ggtttcattt      240
actctaaacc tgtgattcct ctgaattatt ttcatttta agaaattgta tttgttaaat      300
atgtactaca aacttagtag ttggaagggc taattcactc ccaaagaaga caagatatcc      360
ttgatctgtg gatctaccac acacaaggct acttccctga ttagcagaac tacacaccag      420
ggccagggtc agatatccac tgaccttggg atggtgctac aagctagtac cagttgagcc      480
agataaggta gaagaggcca ataaaggaga gaacaccagc ttgttacacc ctgtgagcct      540
gcatgggatg gatgacccgg agagagaagt gttagagtgg aggtttgaca gccgcctagc      600
atttcatcac gtggcccgag agctgcatcc ggagtacttc aagaactgct gatatcgagc      660
ttgctacaag ggactttccg ctggggactt tccaggagg cgtggcctgg gcgggactgg      720
ggagtggcga gccctcagat cctgcatata agcagctgct ttttgcctgt actgggtctc      780
tctggttaga ccagatctga gcctgggagc tctctggcta actagggaac ccactgctta      840
agcctcaata agcttgcctt gagtgcttc aagtagtgtg tgcccgtctg ttgtgtgact      900
ctggtaacta gagatccctc agaccctttt agtcagtgtg aaaatctct agcagtggcg      960 cccgaacagg gacttgaaag cgaaagggaa accagaggag ctctctcgac gcaggactcg     1020
gcttgctgaa gcgcgcacgg caagaggcga ggggcggcga ctggtgagta cgccaaaaat     1080
tttgactagc ggaggctaga aggagagaga tgggtgcgag agcgtcagta ttaagcgggg     1140
gagaattaga tcgatgggaa aaaattcggt taaggccagg gggaaagaaa aaatataaat     1200
taaaacatat agtatgggca agcagggagc tagaacgatt cgcagttaat cctggcctgt     1260
tagaaacatc agaaggctgt agacaaatac tgggacagct acaaccatcc cttcagacag     1320
gatcagaaga acttagatca ttatataata cagtagcaac cctctattgt gtgcatcaaa     1380
ggatagagat aaaagacacc aaggaagctt tagacaagat agaggaagag caaaacaaaa     1440
gtaagaaaaa agcacagcaa gcagcagctg acacaggaca cagcaatcag gtcagccaaa     1500
attaccctat agtgcagaac atccaggggc aaatggtaca tcaggccata tcacctagaa     1560
ctttaaatgc atgggtaaaa gtagtagaag agaaggcttt cagcccagaa gtgataccca     1620
tgttttcagc attatcagaa ggagccaccc cacaagattt aaacaccatg ctaaacacag     1680
tggggggaca tcaagcagcc atgcaaatgt taaaagagac catcaatgag gaagctgcag     1740
aatgggatag agtgcatcca gtgcatgcag ggcctattgc accaggccag atgagagaac     1800
caaggggaag tgacatagca ggaactacta gtacccttca ggaacaaata ggatggatga     1860
caaataatcc acctatccca gtaggagaaa tttataaaag atggataatc ctgggattaa     1920
ataaaatagt aagaatgtat agccctacca gcattctgga cataagacaa ggaccaaaag     1980
aaccctttag agactatgta gaccggttct ataaaactct aagagccgag caagcttcac     2040
aggaggtaaa aaattggatg acagaaacct tgttggtcca aaatgcgaac ccagattgta     2100
agactatttt aaaagcattg ggaccagcgg ctacactaga agaaatgatg acagcatgtc     2160
agggagtagg aggacccggc cataaggcaa gagttttggc tgaagcaatg agccaagtaa     2220
caaattcagc taccataatg atgcagagag gcaattttag gaaccaaaga aagattgtta     2280
agtgtttcaa ttgtggcaaa gaagggcaca cagccagaaa ttgcagggcc cctaggaaaa     2340
agggctgttg gaaatgtgga aaggaaggac accaaatgaa agattgtact gagagacagg     2400 ctaattttt agggaagatc tggccttcct acaagggaag gccagggaat tttcttcaga     2460
```

```
gcagaccaga gccaacagcc ccaccagaag agagcttcag gtctgggta gagacaacaa      2520 ctcccctca gaagcaggag ccgatagaca aggaactgta tcctttaact tccctcagat      2580
cactctttgg caacgacccc tcgtcacaat aaagataggg gggcaactaa aggaagctct     2640
attagataca ggagcagatg atacagtatt agaagaaatg agtttgccag gaagatggaa    2700
accaaaaatg ataggggaa ttggaggttt tatcaaagta agacagtatg atcagatact      2760
catagaaatc tgtggacata aagctatagg tacagtatta gtaggaccta cacctgtcaa   2820
cataattgga agaaatctgt tgactcagat tggttgcact ttaaattttc ccattagccc    2880
tattgagact gtaccagtaa aattaaagcc aggaatggat ggcccaaaag ttaaacaatg    2940
gccattgaca gaagaaaaaa taaaagcatt agtagaaatt tgtacagaga tggaaaagga   3000
agggaaaatt tcaaaaattg ggcctgaaaa tccatacaat actccagtat ttgccataaa   3060
gaaaaaagac agtactaaat ggagaaaatt agtagatttc agagaactta ataagagaac    3120
tcaagacttc tgggaagttc aattaggaat accacatccc gcagggttaa aaagaaaaa    3180 atcagtaaca gtactggatg tgggtgatgc atattttca gttcccttag atgaagactt     3240
caggaaatat actgcattta ccatacctag tataaacaat gagacaccag ggattagata   3300
tcagtacaat gtgcttccac agggatggaa aggatcacca gcaatattcc aaagtagcat    3360
gacaaaaatc ttagagcctt ttagaaaaca aaatccagac atagttatct atcaatacat   3420
ggatgatttg tatgtaggat ctgacttaga aatagggcag catagaacaa aaatagagga   3480
gctgagacaa catctgttga ggtggggact taccacacca gacaaaaaac atcagaaaga    3540
acctccattc ctttggatgg gttatgaact ccatcctgat aaatggacag tacagcctat    3600
agtgctgcca gaaaaagaca gctggactgt caatgacata cagaagttag tgggaaatt     3660 gaattgggca agtcagattt acccagggat taaagtaagg caattatgta aactccttag    3720
aggaaccaaa gcactaacag aagtaatacc actaacagaa gaagcagagc tagaactggc   3780
agaaaacaga gagattctaa aagaaccagt acatggagtg tattatgacc catcaaaaga   3840
cttaatagca gaaatacaga gcaggggca aggccaatgg acatatcaaa tttatcaaga     3900
gccatttaaa aatctgaaaa caggaaaata tgcaagaatg agggtgccc acactaatga      3960 tgtaaaacaa ttaacagagg cagtgcaaaa aataaccaca gaaagcatag taatatgggg    4020
aaagactcct aaatttaaac tgcccataca aaaggaaaca tgggaaacat ggtggacaga    4080
gtattggcaa gccacctgga ttcctgagtg ggagtttgtt aatacccctc ctttagtgaa    4140
attatggtac cagttagaga agaacccat agtaggagca gaaaccttct atgtagatgg     4200
ggcagctaac agggagacta aattaggaaa agcaggatat gttactaata gaggaagaca    4260
aaaagttgtc accctaactg acacaacaaa tcagaagact gagttacaag caatttatct    4320
agctttgcag gattcgggat tagaagtaaa catagtaaca gactcacaat atgcattagg    4380
aatcattcaa gcacaaccag atcaaagtga atcagagtta gtcaatcaaa taatagagca   4440
gttaataaaa aaggaaaagg tctatctggc atgggtacca gcacacaaag gaattggagg    4500
aaatgaacaa gtagataaat tagtcagtgc tggaatcagg aaagtactat ttttagatgg   4560
aatagataag gccaagatg aacatgagaa atatcacagt aattggagag caatggctag     4620
tgattttaac ctgccacctg tagtagcaaa agaaatagta gccagctgtg ataaatgtca    4680
gctaaaagga gaagccatgc atggacaagt agactgtagt ccaggaatat ggcaactaga    4740
ttgtacacat ttagaaggaa aagttatcct ggtagcagtt catgtagcca gtggatatat    4800
agaagcagaa gttattccag cagaaacagg gcaggaaaca gcatattttc ttttaaaatt   4860
```

```
agcaggaaga tggccagtaa aaacaataca tacagacaat ggcagcaatt tcaccagtgc   4920
tacggttaag gccgcctgtt ggtgggcggg aatcaagcag gaatttggaa ttccctacaa   4980
tccccaaagt caaggagtag tagaatctat gaataaagaa ttaaagaaaa ttataggaca   5040
ggtaagagat caggctgaac atcttaagac agcagtacaa atggcagtat tcatccacaa   5100
ttttaaaaga aaagggggga ttgggggggta cagtgcaggg gaaagaatag tagacataat   5160
agcaacagac atacaaacta aagaattaca aaaacaaatt acaaaaattc aaaattttcg   5220
ggtttattac agggacagca gaaatccact ttggaaagga ccagcaaagc tcctctggaa   5280
aggtgaaggg gcagtagtaa tacaagataa tagtgacata aaagtagtgc caagaagaaa   5340
agcaaagatc attagggatt atggaaaaca gatggcaggt gatgattgtg tggcaagtag   5400
acaggatgag gattagaaca tggaaaagtt tagtaaaaca ccatatgtat gtttcaggga   5460
aagctagggg atggttttat agacatcact atgaaagccc tcatccaaga ataagttcag   5520
aagtacacat cccactaggg gatgctagat tggtaataac aacatattgg ggtctgcata   5580
caggagaaag agactggcat ttgggtcagg gagtctccat agaatggagg aaaaagagat   5640
atagcacaca agtagaccct gaactagcag accaactaat tcatctgtat tactttgact   5700
gtttttcaga ctctgctata agaaaggcct tattaggaca catagttagc cctaggtgtg   5760
aatatcaagc aggacataac aaggtaggat ctctacaata cttggcacta gcagcattaa   5820
taacaccaaa aaagataaag ccacctttgc ctagtgttac gaaactgaca gaggatagat   5880
ggaacaagcc ccagaagacc aagggccaca gagggagcca cacaatgaat ggacactaga   5940
gcttttagag gagcttaaga atgaagctgt tagacatttt cctaggattt ggctccatgg   6000
cttagggcaa catatctatg aaacttatgg ggatacttgg gcaggagtgg aagccataat   6060
aagaattctg caacaactgc tgtttatcca ttttcagaat tgggtgtcga catagcagaa   6120
taggcgttac tcgacagagg agagcaagaa atggagccag tagatcctag actagagccc   6180
tggaagcatc caggaagtca gcctaaaact gcttgtacca attgctattg taaaaagtgt   6240
tgctttcatt gccaagtttg tttcataaca aaagccttag gcatctccta tggcaggaag   6300
aagcggagac agcgacgaag agctcatcag aacagtcaga ctcatcaagc ttctctatca   6360
aagcagtaag tagtacatgt aacgcaacct ataccaatag tagcaatagt agcattagta   6420
gtagcaataa taatagcaat agttgtgtgg tccatagtaa tcatagaata taggaaaata   6480
ttaagacaaa gaaaaataga caggttaatt gatagactaa tagaaagagc agaagacagt   6540
ggcaatgaga gtgaaggaga atatcagca cttgtggaga tggggtgga gatgggcac   6600 catgctcctt gggatgttga tgatctgtag tgctacagaa aaattgtggg tcacagtcta   6660
ttatggggta cctgtgtgga aggaagcaac caccactcta ttttgtgcat cagatgctaa   6720
agcatatgat acagaggtac ataatgtttg ggccacacat gcctgtgtac ccacagaccc   6780
caacccacaa gaagtagtat tggtaaatgt gacagaaaat tttaacatgt ggaaaaatga   6840
catggtagaa cagatgcatg aggatataat cagtttatgg gatcaaagcc taaagccatg   6900
tgtaaaatta accccactct gtgttagttt aaagtgcact gatttgaaga atgatactaa   6960
taccaatagt agtagcggga gaatgataat ggagaaagga gagataaaaa actgctcttt   7020
caatatcagc acaagcataa gaggtaaggt gcagaaagaa tatgcatttt tttataaact   7080
tgatataata ccaatagata tgatactac cagctataag ttgacaagtt gtaacacctc   7140
agtcattaca caggcctgtc caaaggtatc ctttgagcca attcccatac attattgtgc   7200
```

```
cccggctggt tttgcgattc taaaatgtaa taataagacg ttcaatggaa caggaccatg   7260
tacaaatgtc agcacagtac aatgtacaca tggaattagg ccagtagtat caactcaact   7320
gctgttaaat ggcagtctag cagaagaaga ggtagtaatt agatctgtca atttcacgga   7380
caatgctaaa accataatag tacagctgaa cacatctgta gaaattaatt gtacaagacc   7440
caacaacaat acaagaaaaa gaatccgtat ccagagagga ccagggagag catttgttac   7500
aataggaaaa ataggaaata tgagacaagc acattgtaac attagtagag caaaatggaa   7560
taacactttt aaacagatag ctagcaaatt aagagaacaa tttggaaata taaaacaat    7620 aatctttaag caatcctcag gaggggaccc agaaattgta acgcacagtt ttaattgtgg   7680
aggggaattt ttctactgta attcaacaca actgtttaat agtacttggt ttaatagtac   7740
ttggagtact gaagggtcaa ataacactga aggaagtgac acaatcaccc tcccatgcag   7800
aataaaacaa attataaaca tgtggcagaa agtaggaaaa gcaatgtatg cccctcccat   7860
cagtggacaa attagatgtt catcaaatat tacagggctg ctattaacaa gagatggtgg   7920
taatagcaac aatgagtccg agatcttcag acctggagga ggagatatga gggacaattg   7980
gagaagtgaa ttatataaat ataaagtagt aaaaattgaa ccattaggag tagcacccac   8040
caaggcaaag agaagagtgg tgcagagaga aaaaagagca gtgggaatag gagctttgtt   8100
ccttgggttc ttgggagcag caggaagcac tatgggcgca gcgtcaatga cgctgacggt   8160
acaggccaga caattattgt ctggtatagt gcagcagcag aacaatttgc tgagggctat   8220
tgaggcgcaa cagcatctgt tgcaactcac agtctggggc atcaagcagc tccaggcaag   8280
aatcctggct gtggaaagat acctaaagga tcaacagctc ctggggattt ggggttgctc   8340
tggaaaactc atttgcacca ctgctgtgcc ttggaatgct agttggagta ataaatctct   8400
ggaacagatt tggaatcaca cgacctggat ggagtgggac agagaaatta acaattacac   8460
aagcttaata cactccttaa ttgaagaatc gcaaaaccag caagaaaaga atgaacaaga   8520
attattggaa ttagataaat gggcaagttt gtggaattgg tttaacataa caaattggct   8580
gtggtatata aaattattca taatgatagt aggaggcttg gtaggtttaa gaatagtttt   8640
tgctgtactt tctatagtga atagagttag cagggatat  tcaccattat cgtttcagac   8700
ccacctccca accccgaggg gacccgacag gcccgaagga atagaagaag aaggtggaga   8760
gagagacaga gacagatcca ttcgattagt gaacggatcc ttagcactta tctgggacga   8820
tctgcggagc ctgtgcctct tcagctacca ccgcttgaga gacttactct tgattgtaac   8880
gaggattgtg gaacttctgg gacgcagggg gtgggaagcc ctcaaatatt ggtggaatct   8940
cctacaatat tggagtcagg agctaaagaa tagtgctgtt agcttgctca atgccacagc   9000
catagcagta gctgagggga cagataggt tatagaagta gtacaaggag cttgtagagc   9060
tattcgccac atacctagaa gaataagaca gggcttggaa aggatttttgc tataagatgg   9120 gtggcgcggc cgcaatggtg agcaagggcg aggagctgtt caccggggtg gtgcccatcc   9180
tggtcgagct ggacggcgac gtaaacggcc acaagttcag cgtgtccggc gagggcgagg   9240
gcgatgccac ctacggcaag ctgaccctga agttcatctg caccaccggc aagctgcccg   9300
tgccctggcc caccctcgtg accccctga cctacggcgt gcagtgcttc agccgctacc   9360
ccgaccacat gaagcagcac gacttcttca gtccgccat gcccgaaggc tacgtccagg   9420
agcgcaccat cttcttcaag gacgacggca actacaagac ccgcgccgag gtgaagttcg   9480
agggcgacac cctggtgaac cgcatcgagc tgaagggcat cgacttcaag gaggacggca   9540
acatcctggg gcacaagctg gagtacaact acaacagcca caacgtctat atcatggccg   9600
```

```
acaagcagaa gaacggcatc aaggcgaact tcaagatccg ccacaacatc gaggacggca    9660
gcgtgcagct cgccgaccac taccagcaga acacccccat cggcgacggc cccgtgctgc    9720
tgcccgacaa ccactacctg agcacccagt ccgccctgag caaagacccc aacgagaagc    9780
gcgatcacat ggtcctgctg gagttcgtga ccgccgccgg gatcactctc ggcatggacg    9840
agctgtacaa gtaagaattc tgactcgaga cctagaaaaa catggagcaa tcacaagtag    9900
caatacagca gctaccaatg ctgattgtgc ctggctagaa gcacaagagg aggaggaggt    9960
gggttttcca gtcacacctc aggtaccttt aagaccaatg acttacaagg cagctgtaga   10020
tcttagccac ttttaaaag aaaaggggg actggaaggg ctaattcact cccaacgaag   10080
acaagatatc cttgatctgt ggatctacca cacacaaggc tacttccctg attggcagaa   10140
ctacacacca gggccaggga tcagatatcc actgaccttt ggatggtgct acaagctagt   10200
accagttgag caagagaagg tagaagaagc caatgaagga gagaacaccc gcttgttaca   10260
ccctgtgagc ctgcatggga tggatgaccc ggagagagaa gtattagagt ggaggtttga   10320
cagccgccta gcatttcatc acatggcccg agagctgcat ccggagtact tcaagaactg   10380
ctgacatcga gcttgctaca agggactttc cgctggggac tttccaggga ggcgtggcct   10440
gggcgggact ggggagtggc gagccctcag atgctgcata taagcagctg cttttttgctt   10500 gtactgggtc tctctggtta gaccagatct gagcctggga gctctctggc taactaggga   10560
acccactgct taagcctcaa taaagcttgc cttgagtgct tcaagtagtg tgtgcccgtc   10620
tgttgtgtga ctctggcgcg cctctagaat taattccgtg tattctatag tgtcacctaa   10680
atcgtatgtg tatgatacat aaggttatgt attaattgta gccgcgttct aacgacaata   10740
tgtacaagcc taattgtgta gcatctggct tactgaagca gacccatcta tctctctcgt   10800
aaactgccgt cagagtcggt ttggttggac gaaccttctg agtttctggt aacgccgtcc   10860
cgcacccgga aatggtcagc gaaccaatca gcagggtcat cgctagccag atcctctacg   10920
ccggacgcat cgtggccggc atcaccggcg ccacaggtgc ggttgctggc gcctatatcg   10980
ccgacatcac cgatggggaa gatcgggctc gccacttcgg gctcatgagc gcttgtttcg   11040
gcgtgggtat ggtggcaggc cccgtggccg ggggactgtt gggcgccatc tccttgcatg   11100
caccattcct tgcggcggcg gtgctcaacg gcctcaacct actactgggc tgcttcctaa   11160
tgcaggagtc gcataaggga gagcgtcgaa tggtgcactc tcagtacaat ctgctctgat   11220
gccgcatagt taagccagcc ccgacacccg ccaacacccg ctgacgcgcc ctgacgggct   11280
tgtctgctcc cggcatccgc ttacagacaa gctgtgaccg tctccgggag ctgcatgtgt   11340
cagaggtttt caccgtcatc accgaaacgc gcgagacgaa agggcctcgt gatacgccta   11400
tttttatagg ttaatgtcat gataataatg gtttcttaga cgtcaggtgg cacttttcgg   11460
ggaaatgtgc gcggaacccc tatttgttta ttttttctaaa tacattcaaa tatgtatccg   11520
ctcatgagac aataaccctg ataaatgctt caataatatt gaaaaggaa gagtatgagt   11580 attcaacatt tccgtgtcgc ccttattccc ttttttgcgg cattttgcct tcctgttttt   11640
gctcacccag aaacgctggt gaaagtaaaa gatgctgaag atcagttggg tgcacgagtg   11700
ggttacatcg aactggatct caacagcggt aagatccttg agagttttcg ccccgaagaa   11760
cgttttccaa tgatgagcac ttttaaagtt ctgctatgtg gcgcggtatt atcccgtatt   11820
gacgccgggc aagagcaact cggtcgccgc atacactatt ctcagaatga cttggttgag   11880
tactcaccag tcacagaaaa gcatcttacg gatggcatga cagtaagaga attatgcagt   11940
```

```
gctgccataa ccatgagtga taacactgcg gccaacttac ttctgacaac gatcggagga    12000
ccgaaggagc taaccgcttt tttgcacaac atgggggatc atgtaactcg ccttgatcgt    12060
tgggaaccgg agctgaatga agccatacca aacgacgagc gtgacaccac gatgcctgta    12120
gcaatggcaa caacgttgcg caaactatta actggcgaac tacttactct agcttcccgg    12180
caacaattaa tagactggat ggaggcggat aaagttgcag gaccacttct gcgctcggcc    12240
cttccggctg gctggtttat tgctgataaa tctggagccg gtgagcgtgg gtctcgcggt    12300
atcattgcag cactggggcc agatggtaag ccctcccgta tcgtagttat ctacacgacg    12360
gggagtcagg caactatgga tgaacgaaat agacagatcg ctgagatagg tgcctcactg    12420
attaagcatt ggtaactgtc agaccaagtt tactcatata ctttagat tgatttaaaa    12480 cttcatttt aatttaaaag gatctaggtg aagatccttt ttgataatct catgaccaaa    12540
atcccttaac gtgagttttc gttccactga gcgtcagacc ccgtagaaaa gatcaaagga    12600
tcttcttgag atcctttttt tctgcgcgta atctgctgct tgcaaacaaa aaaaccaccg    12660
ctaccagcgg tggtttgttt gccggatcaa gagctaccaa ctcttttcc gaaggtaact    12720 ggcttcagca gagcgcagat accaaatact gttcttctag tgtagccgta gttaggccac    12780
cacttcaaga actctgtagc accgcctaca tacctcgctc tgctaatcct gttaccagtg    12840
gctgctgcca gtggcgataa gtcgtgtctt accgggttgg actcaagacg atagttaccg    12900
gataaggcgc agcggtcggg ctgaacgggg gttcgtgca cacagcccag cttggagcga    12960
acgacctaca ccgaactgag atacctacag cgtgagctat gagaaagcgc cacgcttccc    13020
gaagggagaa aggcggacag gtatccggta agcggcaggg tcggaacagg agagcgcacg    13080
agggagcttc cagggggaaa cgcctggtat ctttatagtc ctgtcgggtt tcgccacctc    13140
tgacttgagc gtcgattttt gtgatgctcg tcagggggggc ggagcctatg gaaaaacgcc    13200
agcaacgcgg cctttttacg gttcctggcc ttttgctggc cttttgctca catgttcttt    13260
cctgcgttat cccctgattc tgtggataac cgtattaccg cctttgagtg agctgatacc    13320
gctcgccgca gccgaacgac cgagcgcagc gagtcagtga gcgaggaagc ggaagagcgc    13380
ccaatacgca aaccgcctct ccccgcgcgt tggccgattc attaatgcag ctgtggaatg    13440
tgtgtcagtt agggtgtgga aagtccccag gctccccagc aggcagaagt atgcaaagca    13500
tgcatctcaa ttagtcagca accaggtgtg gaaagtcccc aggctcccca gcaggcagaa    13560
gtatgcaaag catgcatctc aattagtcag caaccatagt cccgccccta actccgccca    13620
tcccgcccct aactccgccc agttccgccc attctccgcc ccatggctga ctaattttt    13680 ttatttatgc agaggccgag gccgcctcgg cctctgagct attccagaag tagtgaggag    13740
gcttttttgg aggcctaggc ttttgcaaaa agcttggaca caagacaggc ttgcgagata    13800
tgtttgagaa taccacttta tcccgcgtca gggagaggca gtgcgtaaaa agacgcggac    13860
tcatgtgaaa tactggtttt tagtgcgcca gatctctata atctcgcgca acctattttc    13920
ccctcgaaca cttttaagc cgtagataaa caggctggga cacttcacat gagcgaaaaa    13980
tacatcgtca cctgggacat gttgcagatc catgcacgta aactcgcaag ccgactgatg    14040
ccttctgaac aatggaaagg cattattgcc gtaagccgtg gcggtctggt accgggtgcg    14100
ttactggcgc gtgaactggg tattcgtcat gtcgataccg tttgtatttc cagctacgat    14160
cacgacaacc agcgcgagct taaagtgctg aaacgcgcag aaggcgatgg cgaaggcttc    14220
atcgttattg atgacctggt ggataccggt ggtactgcgg ttgcgattcg tgaaatgtat    14280
ccaaaagcgc actttgtcac catcttcgca aaaccggctg gtcgtccgct ggttgatgac    14340
```

```
tatgttgttg atatcccgca agatacctgg attgaacagc cgtgggatat gggcgtcgta    14400
ttcgtcccgc caatctccgg tcgctaatct tttcaacgcc tggcactgcc gggcgttgtt    14460 cttttaact tcaggcgggt tacaatagtt tccagtaagt attctggagg ctgcatccat     14520
gacacaggca aacctgagcg aaaccctgtt caaaccccgc tttaaacatc ctgaaacctc    14580
gacgctagtc cgccgcttta atcacggcgc acaaccgcct gtgcagtcgg cccttgatgg    14640
taaaaccatc cctcactggt atcgcatgat taaccgtctg atgtggatct ggcgcggcat    14700
tgacccacgc gaaatcctcg acgtccaggc acgtattgtg atgagcgatg ccgaacgtac    14760
cgacgatgat ttatacgata cggtgattgg ctaccgtggc ggcaactgga tttatgagtg    14820
ggccccggat ctttgtgaag gaaccttact tctgtggtgt gacataattg gacaaactac    14880
ctacagagat ttaaagctct aaggtaaata taaaattttt aagtgtataa tgtgttaaac    14940
tactgattct aattgtttgt gtattttaga ttccaaccta tggaactgat gaatgggagc    15000
agtggtggaa tgcctttaat gaggaaaacc tgttttgctc agaagaaatg ccatctagtg    15060
atgatgaggc tactgctgac tctcaacatt ctactcctcc aaaaaagaag agaaaggtag    15120
aagaccccaa ggactttcct tcagaattgc taagttttt gagtcatgct gtgtttagta    15180
atagaactct tgcttgcttt gctatttaca ccacaaagga aaagctgca ctgctataca     15240 agaaaattat ggaaaaatat tctgtaacct ttataagtag gcataacagt tataatcata    15300
acatactgtt ttttcttact ccacacaggc atagagtgtc tgctattaat aactatgctc    15360
aaaaattgtg tacctttagc tttttaattt gtaaagggt taataaggaa tatttgatgt     15420
atagtgcctt gactagagat cataatcagc cataccacat ttgtagaggt tttacttgct    15480
ttaaaaaacc tcccacacct cccctgaac ctgaaacata aaat                      15524
```

<210> SEQ ID NO 6
<211> LENGTH: 14226
<212> TYPE: DNA
<213> ORGANISM: Human immunodeficiency virus type 1

<400> SEQUENCE: 6

```
gaatgcaatt gttgttgtta acttgtttat tgcagcttat aatggttaca ataaagcaa      60 tagcatcaca aatttcacaa ataaagcatt ttttcactg cattctagtt gtggtttgtc    120
caaactcatc aatgtatctt atcatgtctg gatcaactgg ataactcaag ctaaccaaaa    180
tcatcccaaa cttcccaccc cataccctat taccactgcc aattacctgt ggtttcattt    240
actctaaacc tgtgattcct ctgaattatt ttcattttaa agaaattgta tttgttaaat    300
atgtactaca aacttagtag ttggaagggc taattcactc ccaaagaaga caagatatcc    360
ttgatctgtg gatctaccac acacaaggct acttccctga ttagcagaac tacacaccag    420
ggccagggtc agatatccac tgacctttgg atggtgctac aagctagtac cagttgagcc    480
agataaggta agagaggcca ataaggaga aacaccagc ttgttacacc ctgtgagcct      540
gcatgggatg gatgacccgg agagagaagt gttagagtgg aggtttgaca gccgcctagc    600
atttcatcac gtggcccgag agctgcatcc ggagtacttc aagaactgct gatatcgagc    660
ttgctacaag ggactttccg ctggggactt tccaggagg cgtggcctgg gcgggactgg     720
ggagtggcga gccctcagat cctgcatata agcagctgct ttttgcctgt actgggtctc    780
tctggttaga ccagatctga gcctgggagc tctctggcta actagggaac ccactgctta    840
agcctcaata aagcttgcct tgagtgcttc aagtagtgtg tgcccgtctg ttgtgtgact    900
```

```
ctggtaacta gagatccctc agacccttt  agtcagtgtg gaaaatctct agcagtggcg    960
cccgaacagg gacttgaaag cgaaagggaa accagaggag ctctctcgac gcaggactcg   1020
gcttgctgaa gcgcgcacgg caagaggcga ggggcggcga ctggtgagta cgccaaaaat   1080
tttgactagc ggaggctaga aggagagaga tgggtgcgag agcgtcagta ttaagcgggg   1140
gagaattaga tcgatgggaa aaaattcggt taaggccagg gggaagaaaa aatataaat    1200
taaaacatat agtatgggca agcagggagc tagaacgatt cgcagttaat cctggcctgt   1260
tagaaacatc agaaggctgt agacaaatac tgggacagct acaaccatcc cttcagacag   1320
gatcagaaga acttagatca ttatataata cagtagcaac cctctattgt gtgcatcaaa   1380
ggatagagat aaaagacacc aaggaagctt tagacaagat agaggaagag caaaacaaaa   1440
gtaagaaaaa agcacagcaa gcagcagctg acacaggaca cagcaatcag gtcagccaaa   1500
attaccctat agtgcagaac atccaggggc aaatggtaca tcaggccata tcacctagaa   1560
ctttaaatgc atgggtaaaa gtagtagaag agaaggcttt cagcccagaa gtgataccca   1620
tgttttcagc attatcagaa ggagccaccc cacaagattt aaacaccatg ctaaacacag   1680
tggggggaca tcaagcagcc atgcaaatgt taaaagagac catcaatgag gaagctgcag   1740
aatgggatag agtgcatcca gtgcatgcag ggcctattgc accaggccag atgagagaac   1800
caaggggaag tgacatagca ggaactacta gtacccttca ggaacaaata ggatggatga   1860
caaataatcc acctatccca gtaggagaaa tttataaaag atggataatc ctgggattaa   1920
ataaaatagt aagaatgtat agccctacca gcattctgga cataagacaa ggaccaaaag   1980
aacccttag  agactatgta gaccggttct ataaaactct aagagccgag caagcttcac   2040
aggaggtaaa aaattggatg acagaaacct tgttggtcca aaatgcgaac ccagattgta   2100
agactatttt aaaagcattg ggaccagcgg ctacactaga agaaatgatg acagcatgtc   2160
agggagtagg aggacccggc cataaggcaa gagttttggc tgaagcaatg agccaagtaa   2220
caaattcagc taccataatg atgcagagag gcaattttag gaaccaaaga aagattgtta   2280
agtgtttcaa ttgtggcaaa gaagggcaca cagccagaaa ttgcagggcc cctaggaaaa   2340
agggctgttg gaaatgtgga aaggaaggac accaaatgaa agattgtact gagagacagg   2400
ctaattttt  agggaagatc tggccttcct acaagggaag gccagggaat tttcttcaga   2460
gcagaccaga gccaacagcc ccaccagaag agagcttcag gtctggggta gagacaacaa   2520
ctccccctca gaagcaggag ccgatagaca aggaactgta tcctttaact tccctcagat   2580
cactctttgg caacgacccc tcgtcacaat aaagataggg gggcaactaa aggaagctct   2640
attagataca ggagcagatg atacagtatt agaagaaatg agtttgccag gaagatggaa   2700
accaaaaatg atagggggaa ttggaggttt tatcaaagta agacagtatg atcagatact   2760
catagaaatc tgtggacata aagctatagg tacagtatta gtaggaccta cacctgtcaa   2820
cataattgga agaaatctgt tgactcagat tggttgcact ttaaattttc ccattagccc   2880
tattgagact gtaccagtaa aattaaagcc aggaatggat ggcccaaaag ttaaacaatg   2940
gccattgaca gaagaaaaaa taaaagcatt agtagaaatt tgtacagaga tggaaaagga   3000
agggaaaatt tcaaaaattg ggcctgaaaa tccatacaat actccagtat ttgccataaa   3060
gaaaaaagac agtactaaat ggagaaaatt agtagatttc agagaactta ataagagaac   3120
tcaagacttc tgggaagttc aattaggaat accacatccc gcagggttaa aaaagaaaaa   3180
atcagtaaca gtactggatg tgggtgatgc atatttttca gttcccttag atgaagactt   3240
caggaaatat actgcattta ccatacctag tataaacaat gagacaccag ggattagata   3300
```

```
tcagtacaat gtgcttccac agggatggaa aggatcacca gcaatattcc aaagtagcat    3360
gacaaaaatc ttagagcctt ttagaaaaca aaatccagac atagttatct atcaatacat    3420
ggatgatttg tatgtaggat ctgacttaga aatagggcag catagaacaa aaatagagga    3480
gctgagacaa catctgttga ggtggggact taccacacca gacaaaaaac atcagaaaga    3540
acctccattc ctttggatgg gttatgaact ccatcctgat aaatggacag tacagcctat    3600
agtgctgcca gaaaaagaca gctggactgt caatgacata cagaagttag tggggaaatt    3660
gaattgggca agtcagattt acccagggat taaagtaagg caattatgta aactccttag    3720
aggaaccaaa gcactaacag aagtaatacc actaacagaa gaagcagagc tagaactggc    3780
agaaaacaga gagattctaa aagaaccagt acatggagtg tattatgacc catcaaaaga    3840
cttaatagca gaaatacaga agcaggggca aggccaatgg acatatcaaa tttatcaaga    3900
gccatttaaa aatctgaaaa caggaaaata tgcaagaatg aggggtgccc acactaatga    3960
tgtaaaacaa ttaacagagg cagtgcaaaa aataaccaca gaaagcatag taatatgggg    4020
aaagactcct aaatttaaac tgcccataca aaaggaaaca tgggaaacat ggtggacaga    4080
gtattggcaa gccacctgga ttcctgagtg ggagtttgtt aatacccctc ctttagtgaa    4140
attatggtac cagttagaga agaacccat agtaggagca gaaaccttct atgtagatgg    4200
ggcagctaac agggagacta aattaggaaa agcaggatat gttactaata gaggaagaca    4260
aaaagttgtc accctaactg acacaacaaa tcagaagact gagttacaag caatttatct    4320
agctttgcag gattcgggat tagaagtaaa catagtaaca gactcacaat atgcattagg    4380
aatcattcaa gcacaaccag atcaaagtga atcagagtta gtcaatcaaa taatagagca    4440
gttaataaaa aaggaaaagg tctatctggc atgggtacca gcacacaaag gaattggagg    4500
aaatgaacaa gtagataaat tagtcagtgc tggaatcagg aaagtactat ttttagatgg    4560
aatagataag gcccaagatg aacatgagaaa atatcacagt aattggagag caatggctag    4620
tgattttaac ctgccacctg tagtagcaaa agaaatagta gccagctgtg ataaatgtca    4680
gctaaaagga gaagccatgc atggacaagt agactgtagt ccaggaatat ggcaactaga    4740
ttgtacacat ttagaaggaa aagttatcct ggtagcagtt catgtagcca gtggatatat    4800
agaagcagaa gttattccag cagaaacagg gcaggaaaca gcatattttc ttttaaaatt    4860
agcaggaaga tggccagtaa aaacaataca tacagacaat ggcagcaatt tcaccagtgc    4920
tacggttaag gccgcctgtt ggtgggcggg aatcaagcag gaatttggaa ttccctacaa    4980
tccccaaagt caaggagtag tagaatctat gaataaagaa ttaaagaaaa ttataggaca    5040
ggtaagagat caggctgaac atcttaagac agcagtacaa atggcagtat tcatccacaa    5100
ttttaaaaga aaagggggga ttggggggta cagtgcaggg gaaagaatag tagacataat    5160
agcaacagac atacaaacta agaattaca aaacaaatt acaaaaattc aaaattttcg    5220
ggtttattac agggacagca gaaatccact ttggaaagga ccagcaaagc tcctctggaa    5280
aggtgaaggg gcagtagtaa tacaagataa tagtgacata aaagtagtgc caagaagaaa    5340
agcaaagatc attagggatt atggaaaaca gatggcaggt gatgattgtg tggcaagtag    5400
acaggatgag gattagaaca tggaaaagtt tagtaaaaca ccatatgtat gtttcaggga    5460
aagctagggg atggttttat agacatcact atgaaagccc tcatccaaga ataagttcag    5520
aagtacacat cccactaggg gatgctagat tggtaataac aacatattgg ggtctgcata    5580
caggagaaag agactggcat ttgggtcagg gagtctccat agaatggagg aaaaagagat    5640
```

```
atagcacaca agtagaccct gaactagcag accaactaat tcatctgtat tactttgact    5700 gttttttcaga ctctgctata agaaaggcct tattaggaca catagttagc cctaggtgtg    5760
aatatcaagc aggacataac aaggtaggat ctctacaata cttggcacta gcagcattaa    5820
taacaccaaa aaagataaag ccacctttgc ctagtgttac gaaactgaca gaggatagat    5880
ggaacaagcc ccagaagacc aagggccaca gagggagcca cacaatgaat ggacactaga    5940
gcttttagag gagcttaaga atgaagctgt tagacatttt cctaggattt ggctccatgg    6000
cttagggcaa catatctatg aaacttatgg ggatacttgg gcaggagtgg aagccataat    6060
aagaattctg caacaactgc tgtttatcca ttttcagaat tgggtgtcga catagcagaa    6120
taggcgttac tcgacagagg agagcaagaa atggagccag tagatcctag actagagccc    6180
tggaagcatc caggaagtca gcctaaaact gcttgtacca attgctattg taaaaagtgt    6240
tgctttcatt gccaagtttg tttcataaca aaagccttag gcatctccta tggcaggaag    6300
aagcggagac agcgacgaag agctcatcag aacagtcaga ctcatcaagc ttctctatca    6360
aagcagtaag tagtacatgt aacgcaacct ataccaatag tagcaatagt agcattagta    6420
gtagcaataa taatagcaat agttgtgtgg tccatagtaa tcatagaata taggaaaata    6480
ttaagacaaa gaaaaataga caggttaatt gatagactaa tagaaagagc agaagacagt    6540
ggcatacgta tgcccctccc atcagtggac aaattagatg ttcatcaaat attacagggc    6600
tgctattaac aagagatggt ggtaatagca acaatgagtc cgagatcttc agacctggag    6660
gaggagatat gagggacaat tggagaagtg aattatataa atataaagta gtaaaaattg    6720
aaccattagg agtagcaccc accaaggcaa agagaagagt ggtgcagaga gaaaaaagag    6780
cagtgggaat aggagctttg ttccttgggt tcttgggagc agcaggaagc actatgggcg    6840
cagcgtcaat gacgctgacg gtacaggcca gacaattatt gtctggtata gtgcagcagc    6900
agaacaattt gctgagggct attgaggcgc aacagcatct gttgcaactc acagtctggg    6960
gcatcaagca gctccaggca agaatcctgg ctgtggaaag atacctaaag gatcaacagc    7020
tcctggggat ttggggttgc tctggaaaac tcatttgcac cactgctgtg ccttggaatg    7080
ctagttggag taataaatct ctggaacaga tttggaatca cacgacctgg atggagtggg    7140
acagagaaat taacaattac acaagcttaa tacactcctt aattgaagaa tcgcaaaacc    7200
agcaagaaaa gaatgaacaa gaattattgg aattagataa atgggcaagt ttgtggaatt    7260
ggtttaacat aacaaattgg ctgtggtata taaaattatt cataatgata gtaggaggct    7320
tggtaggttt aagaatagtt tttgctgtac tttctatagt gaatagagtt aggcagggat    7380
attcaccatt atcgtttcag acccacctcc caacccccgag gggacccgac aggcccgaag    7440
gaatagaaga agaaggtgga gagagagaca gagacagatc cattcgatta gtgaacggat    7500
ccttagcact tatctgggac gatctgcgga gcctgtgcct cttcagctac caccgcttga    7560
gagacttact cttgattgta acgaggattg tggaacttct gggacgcagg gggtgggaag    7620
ccctcaaata ttggtggaat ctcctacaat attggagtca ggagctaaag aatagtgctg    7680
ttagcttgct caatgccaca gccatagcag tagctgaggg gacagatagg gttatagaag    7740
tagtacaagg agcttgtaga gctattcgcc acatacctag aagaataaga cagggcttgg    7800
aaaggatttt gctataagat gggtggcgcg gccgcaatgg tgagcaaggg cgaggagctg    7860
ttcaccgggg tggtgcccat cctggtcgag ctggacggcg acgtaaacgg ccacaagttc    7920
agcgtgtccg gcgagggcga gggcgatgcc acctacggca agctgaccct gaagttcatc    7980
tgcaccaccg gcaagctgcc cgtgccctgg cccaccctcg tgaccaccct gacctacggc    8040
```

```
gtgcagtgct tcagccgcta ccccgaccac atgaagcagc acgacttctt caagtccgcc    8100
atgcccgaag gctacgtcca ggagcgcacc atcttcttca aggacgacgg caactacaag    8160
acccgcgccg aggtgaagtt cgagggcgac accctggtga accgcatcga gctgaagggc    8220
atcgacttca aggaggacgg caacatcctg gggcacaagc tggagtacaa ctacaacagc    8280
cacaacgtct atatcatggc cgacaagcag aagaacggca tcaaggcgaa cttcaagatc    8340
cgccacaaca tcgaggacgg cagcgtgcag ctcgccgacc actaccagca gaacaccccc    8400
atcggcgacg gccccgtgct gctgcccgac aaccactacc tgagcaccca gtccgccctg    8460
agcaaagacc ccaacgagaa gcgcgatcac atggtcctgc tggagttcgt gaccgccgcc    8520
gggatcactc tcggcatgga cgagctgtac aagtaagaat tctgactcga gacctagaaa    8580
aacatggagc aatcacaagt agcaatacag cagctaccaa tgctgattgt gcctggctag    8640
aagcacaaga ggaggaggag gtgggttttc cagtcacacc tcaggtacct ttaagaccaa    8700
tgacttacaa ggcagctgta gatcttagcc actttttaaa agaaaagggg ggactggaag    8760
ggctaattca ctcccaacga agacaagata tccttgatct gtggatctac cacacacaag    8820
gctacttccc tgattggcag aactacacac cagggccagg gatcagatat ccactgacct    8880
ttggatggtg ctacaagcta gtaccagttg agcaagagaa ggtagaagaa gccaatgaag    8940
gagagaacac ccgcttgtta caccctgtga gcctgcatgg gatggatgac ccggagagag    9000
aagtattaga gtggaggttt gacagccgcc tagcatttca tcacatggcc cgagagctgc    9060
atccggagta cttcaagaac tgctgacatc gagcttgcta caagggactt tccgctgggg    9120
actttccagg gaggcgtggc ctgggcggga ctggggagtg gcgagccctc agatgctgca    9180
tataagcagc tgcttttgc ttgtactggg tctctctggt tagaccagat ctgagcctgg    9240
gagctctctg gctaactagg gaacccactg cttaagcctc aataaagctt gccttgagtg    9300
cttcaagtag tgtgtgcccg tctgttgtgt gactctggcg cgcctctaga attaattccg    9360
tgtattctat agtgtcacct aaatcgtatg tgtatgatac ataaggttat gtattaattg    9420
tagccgcgtt ctaacgacaa tatgtacaag cctaattgtg tagcatctgg cttactgaag    9480 cagacctat catctctctc gtaaactgcc gtcagagtcg gtttggttgg acgaaccttc    9540
tgagtttctg gtaacgccgt cccgcacccg gaaatggtca gcgaaccaat cagcagggtc    9600
atcgctagcc agatcctcta cgccggacgc atcgtggccg gcatcaccgg cgccacaggt    9660
gcggttgctg gcgcctatat cgccgacatc accgatgggg aagatcgggc tcgccacttc    9720
gggctcatga gcgcttgttt cggcgtgggt atggtggcag gccccgtggc cgggggactg    9780
ttgggcgcca tctccttgca tgcaccattc cttgcggcgg cggtgctcaa cggcctcaac    9840
ctactactgg gctgcttcct aatgcaggag tcgcataagg gagagcgtcg aatggtgcac    9900
tctcagtaca atctgctctg atgccgcata gttaagccag ccccgacacc cgccaacacc    9960
cgctgacgcg ccctgacggg cttgtctgct cccggcatcc gcttacagac aagctgtgac   10020
cgtctccggg agctgcatgt gtcagaggtt ttcaccgtca tcaccgaaac gcgcgagacg   10080
aaagggcctc gtgatacgcc tatttttata ggttaatgtc atgataataa tggtttctta   10140
gacgtcaggt ggcactttc ggggaaatgt gcgcggaacc cctatttgtt tatttttcta   10200
aatacattca aatatgtatc cgctcatgag acaataaccc tgataaatgc ttcaataata   10260
ttgaaaaagg aagagtatga gtattcaaca tttccgtgtc gcccttattc ccttttttgc   10320
ggcattttgc cttcctgttt ttgctcaccc agaaacgctg gtgaaagtaa aagatgctga   10380
```

```
agatcagttg ggtgcacgag tgggttacat cgaactggat ctcaacagcg gtaagatcct   10440
tgagagtttt cgccccgaag aacgttttcc aatgatgagc acttttaaag ttctgctatg   10500
tggcgcggta ttatcccgta ttgacgccgg gcaagagcaa ctcggtcgcc gcatacacta   10560
ttctcagaat gacttggttg agtactcacc agtcacagaa aagcatctta cggatggcat   10620
gacagtaaga gaattatgca gtgctgccat aaccatgagt gataacactg cggccaactt   10680
acttctgaca cgatcggag gaccgaagga gctaaccgct tttttgcaca catgggggga   10740
tcatgtaact cgccttgatc gttgggaacc ggagctgaat gaagccatac caaacgacga   10800
gcgtgacacc acgatgcctg tagcaatggc aacaacgttg cgcaaactat taactggcga   10860
actacttact ctagcttccc ggcaacaatt aatagactgg atggaggcgg ataaagttgc   10920
aggaccactt ctgcgctcgg cccttccggc tggctggttt attgctgata atctggagc    10980
cggtgagcgt gggtctcgcg gtatcattgc agcactgggg ccagatggta agccctcccg   11040
tatcgtagtt atctacacga cggggagtca ggcaactatg gatgaacgaa atagacagat   11100
cgctgagata ggtgcctcac tgattaagca ttggtaactg tcagaccaag tttactcata   11160
tatactttag attgatttaa aacttcattt taatttaaaa aggatctagg tgaagatcct   11220
ttttgataat ctcatgacca aaatccctta acgtgagttt tcgttccact gagcgtcaga   11280
ccccgtagaa aagatcaaag gatcttcttg agatcctttt tttctgcgcg taatctgctg   11340
cttgcaaaca aaaaaaccac cgctaccagc ggtggtttgt ttgccggatc aagagctacc   11400
aactcttttt ccgaaggtaa ctggcttcag cagagcgcag ataccaaata ctgttcttct   11460
agtgtagccg tagttaggcc accacttcaa gaactctgta gcaccgccta catcctcgc    11520
tctgctaatc ctgttaccag tggctgctgc cagtggcgat aagtcgtgtc ttaccgggtt   11580
ggactcaaga cgatagttac cggataaggc gcagcggtcg ggctgaacgg ggggttcgtg   11640
cacacagccc agcttggagc gaacgaccta caccgaactg agatacctac agcgtgagct   11700
atgagaaagc gccacgcttc ccgaagggag aaaggcggac aggtatccgg taagcggcag   11760
ggtcggaaca ggagagcgca cgagggagct tccaggggga aacgcctggt atctttatag   11820
tcctgtcggg tttcgccacc tctgacttga gcgtcgattt ttgtgatgct cgtcaggggg   11880
gcggagccta tggaaaaacg ccagcaacgc ggcctttta cggttcctgg ccttttgctg    11940
gccttttgct cacatgttct ttcctgcgtt atccctgat tctgtggata accgtattac    12000
cgcctttgag tgagctgata ccgctcgccg cagccgaacg accgagcgca gcgagtcagt   12060
gagcgaggaa gcggaagagc gcccaatacg caaaccgcct ctccccgcgc gttggccgat   12120
tcattaatgc agctgtggaa tgtgtgtcag ttagggtgtg gaaagtcccc aggctcccca   12180
gcaggcagaa gtatgcaaag catgcatctc aattagtcag caaccaggtg tggaaagtcc   12240
ccaggctccc cagcaggcag aagtatgcaa agcatgcatc tcaattagtc agcaaccata   12300
gtcccgcccc taactccgcc catcccgccc ctaactccgc ccagttccgc ccattctccg   12360
ccccatggct gactaatttt ttttatttat gcagaggccg aggccgcctc ggcctctgag   12420
ctattccaga agtagtgagg aggcttttt ggaggcctag gcttttgcaa aaagcttgga    12480
cacaagacag gcttgcgaga tatgtttgag aataccactt tatcccgcgt cagggagagg   12540
cagtgcgtaa aaagacgcgg actcatgtga atactggtt tttagtgcgc cagatctcta    12600
taatctcgcg caacctattt tcccctcgaa cacttttaa gccgtagata aacaggctgg   12660
gacacttcac atgagcgaaa aatacatcgt cacctgggac atgttgcaga tccatgcacg   12720
taaactcgca agccgactga tgccttctga acaatggaaa ggcattattg ccgtaagccg   12780
```

```
tggcggtctg gtaccgggtg cgttactggc gcgtgaactg ggtattcgtc atgtcgatac    12840
cgtttgtatt tccagctacg atcacgacaa ccagcgcgag cttaaagtgc tgaaacgcgc    12900
agaaggcgat ggcgaaggct tcatcgttat tgatgacctg gtggataccg gtggtactgc    12960
ggttgcgatt cgtgaaatgt atccaaaagc gcactttgtc accatcttcg caaaaccggc    13020
tggtcgtccg ctggttgatg actatgttgt tgatatcccg caagatacct ggattgaaca    13080
gccgtgggat atgggcgtcg tattcgtccc gccaatctcc ggtcgctaat cttttcaacg    13140
cctggcactg ccgggcgttg ttcttttttaa cttcaggcgg gttacaatag tttccagtaa    13200
gtattctgga ggctgcatcc atgacacagg caaacctgag cgaaaccctg ttcaaacccc    13260
gctttaaaca tcctgaaacc tcgacgctag tccgccgctt taatcacggc gcacaaccgc    13320
ctgtgcagtc ggcccttgat ggtaaaacca tccctcactg gtatcgcatg attaaccgtc    13380
tgatgtggat ctggcgcggc attgacccac gcgaaatcct cgacgtccag gcacgtattg    13440
tgatgagcga tgccgaacgt accgacgatg atttatacga tacggtgatt ggctaccgtg    13500
gcggcaactg gatttatgag tgggccccgg atctttgtga aggaaccttta cttctgtggt    13560 gtgacataat tggacaaact acctacagag atttaaagct ctaaggtaaa tataaaattt    13620
ttaagtgtat aatgtgttaa actactgatt ctaattgttt gtgtatttta gattccaacc    13680
tatggaactg atgaatggga gcagtggtgg aatgccttta atgaggaaaa cctgttttgc    13740
tcagaagaaa tgccatctag tgatgatgag gctactgctg actctcaaca ttctactcct    13800
ccaaaaaaga agagaaaggt agaagacccc aaggactttc cttcagaatt gctaagtttt    13860
ttgagtcatg ctgtgtttag taatagaact cttgcttgct ttgctattta caccacaaag    13920
gaaaaagctg cactgctata caagaaaatt atggaaaaat attctgtaac ctttataagt    13980
aggcataaca gttataatca taacatactg tttttttctta ctccacacag gcatagagtg    14040
tctgctatta ataactatgc tcaaaaattg tgtacctta gctttttaat ttgtaaaggg     14100
gttaataagg aatatttgat gtatagtgcc ttgactagag atcataatca gccataccac    14160
atttgtagag gttttacttg ctttaaaaaa cctcccacac ctcccccctga acctgaaaca    14220 taaaat                                                              14226
```

QUANTITATIVE HIV PHENOTYPE OR TROPISM ASSAY

CROSS REFERENCE TO RELATED APPLICATIONS

This application is a national stage of International Application No. PCT/EP2007/051035 filed Feb. 2, 2007, which claims priority to European Patent Application No. 06101294 filed Feb. 3, 2006 and European Patent Application No. 06115363.1 filed Jun. 13, 2006. The complete disclosures of the aforementioned related patent application are hereby incorporated herein by reference for all purposes.

BRIEF SUMMARY

The present invention relates to a method for prediction of a quantitative phenotype, e.g. gag phenotype, integrase phenotype or tropism in a patient infected by Human Immunodeficiency Virus (HIV).

The human immunodeficiency virus, commonly called HIV, is a retrovirus that primarily infects vital components of the human immune system such as CD4+ T cells, macrophages and dendritic cells. HIV even, directly or indirectly, destroys CD4+ T cells. When enough CD4+ cells have been destroyed by HIV, the immune system barely works, which leads to AIDS (Acquired ImmunoDeficiency Syndrome). Further, HIV directly attacks organs, such as the kidneys, the heart and the brain, leading to acute renal failure, cardiomyopathy, dementia and encephalopathy. Many of the problems faced by people infected with HIV, result from the failure of the immune system to protect them from opportunistic infections and cancers.

AIDS is thought to have originated in sub-Saharan Africa during the twentieth century and it is now a global epidemic. At the end of 2004, UNAIDS estimated that nearly 40 million people were living with HIV. The World Health Organization estimated that the AIDS epidemic had claimed more than 3 million people and that 5 million people had acquired HIV in the same year. Currently it is estimated that 28 million people have died and that it is set to infect 90 million Africans alone, resulting in a minimum estimate of 18 million orphans in the African continent alone.

To infect a cell, a virus must first be able to enter it. HIV is an enveloped virus and accomplishes cell entry by fusing the viral membrane with the cellular plasma membrane. This process is carried out by the viral envelope proteins gp120 and gp41, which are synthesized as a single 160 kD protein before cleavage. The products of this cleavage remain associated until the process of viral entry into the cell begins. gp120 binds to CD4 on CD4+ T lymphocytes and cells of the monocyte/macrophage lineage. This binding event and further interaction between gp120 and cellular co-receptors lead to gp120 dissociation from gp41. The dissociation of gp120 occurs as part of a conformational change in gp41 that leaves it in a "fusion-active" form. This form of gp41 can then mediate fusion between the cellular and viral membranes.

The primary cellular receptor for HIV entry is CD4. However, expression of CD4 on a target cell is necessary but not sufficient for HIV entry and infection. Several chemokine receptors act as co-factors that allow HIV entry when co-expressed with CD4 on a cell surface.

CCR5 and CXCR4 are the major chemokine co-receptors used by HIV to enter into human cells. Based on this co-receptor usage, a new HIV classification was established in 1998, i.e., CCR5-tropic (R5), CXCR4-tropic (X4), or dual tropic (R5/X4) HIV strains. Several years earlier a relationship between viral phenotype (i.e., non-syncytium-inducing, NSI or syncytium-inducing, SI) and the virulence of HIV strains had been identified.

Current knowledge show that, in vitro, R5 viruses usually correspond to NSI on T-cell lines and are able to replicate in monocyte-macrophages (M-tropic), all features previously linked to less virulent strains. In contrast, X4 strains are SI on T-cell lines and replicate preferably on T lymphocytes (T-tropic), all characteristics of more pathogenic virus strains. Based on this knowledge it is believed that HIV co-receptor usage is associated with disease progression.

The first of these co-factors to be identified was CXCR4, or fusin, which is expressed on T cells (Feng et al., HIV-1 entry cofactor: functional cDNA cloning of a seven-transmembrane, G protein-coupled receptor. Science 1996 May 10; 272 (5263):872-877.) Co-expression of CXCR4 and CD4 on a cell allow T-tropic HIV isolates to fuse with and infect the cell. CXCR4 is expressed on many T cells, but usually not on macrophages and hence does not allow fusion with macrophage-tropic (M-tropic) HIV isolates (Feng et al., 1996).

Shortly after the identification of CXCR4, another co-receptor was identified. CCR5, which is expressed on macrophages and on some populations of T cells, can also function in concert with CD4 to allow HIV membrane fusion (Deng et al., Identification of a major co-receptor for primary isolates of HIV-1. Nature 1996 Jun. 20; 381(6584):661-6.) HIV gp120 binding to CCR5 is CD4-dependent, as antibody inhibition of CD4 can reduce binding to CCR5 by 87% (Trkola et al., CD4-dependent, antibody-sensitive interactions between HIV-1 and its co-receptor CCR-5. Nature 1996 Nov. 14; 384(6605):184-7). M-tropic HIV isolates appear to use CCR5 as their co-receptor for infection both of macrophages and of some T cells.

The existence of these two larger receptors of HIV, known as CCR5 and CXCR4 as mentioned above, means that the different viral variants are classified into three categories: R5, X4 and R5X4 in line with their capacity to enter the cell by one of the two receptors exclusively or by both receptors.

CCR5 and CXCR4 belong to the seven-transmembrane G protein-coupled receptor family. They present an α-helix structure composed of four transmembrane domains, three extracellular loops and one N-terminal domain. The CD4-gp120 complex binds to co-receptors through the V3 variable domain of gp120, although other gp120 regions such as V1/V2 and C4 are also involved in this interaction. However, the amino acid sequence of V3 seems to be the major determinant of CCR5 or CXCR4 usage.

The term viral tropism refers to the cell type that the virus infects and replicates in. Nowadays, determination of viral tropism is not performed as a diagnostic test but it does represent a highly useful parameter in certain areas of HIV research. Furthermore, the introduction of specific drugs targeting HIV entry, and more specifically targeting the co-receptors CCR5 or CXCR4, implies that characterization of the viral tropism of an HIV-infected patient will become very important before starting treatment.

Co-receptor antagonists constitute a promising new class of anti-HIV-1 drugs, with several lead compounds being currently in full clinical development.

Several assays have been developed to determine HIV tropism. At the moment it remains unclear which is the most convenient and reliable method.

The MT-2 assay was widely used during the late 1980s to test the cytopathic effect of HIV isolates and served to establish the classification of HIV strains into SI and NSI viruses. The MT-2 cell assay is based on the unique expression of CXCR4 but not CCR5 on the surface of those cells. The main disadvantage though is the need for viral stocks from stimulated patient PBMC (Peripheral Blood Mononuclear Cell). The MT-2 assay may not be the most appropriate for use in patients being treated with co-receptor antagonists.

Another tool for viral tropism determination is the use of recombinant virus tropism assays such as Phenoscript (VI-Ralliance, Paris) and PhenoSense (Monogram Biosciences, San Francisco). Both assays amplify the HIV-1 envelope glycoprotein gene sequence from patient's plasma samples to produce either replication-competent or replication-defective recombinant viruses, respectively. These viruses are then used to infect cell lines that express CD4 in combination with either CCR5 or CXCR4 co-receptors, which permits determination of viral tropism. The severe limitation of these assays is the threshold for detection of X4 viruses in mixed population (R5+X4) i.e., the threshold for detection of minority quasispecies in the presence of mixed viral populations.

This limitation might have important implications in patients undergoing treatment with CCR5 antagonists, in whom emergence of X4 viruses present as a minor population at baseline could be favoured.

Testing for co-receptor utilization (or tropism) prior to initiating therapy with a CCR5 antagonist will be critical to avoid the use of these compounds in patients that are infected with CXCR4 or dual tropic strains.

The molecular basis of HIV tropism is still under investigation, although some investigators showed that probably the V3 loop of the gp120 envelope protein could be involved. There were efforts made to identify which residues within the V3 domain could be involved in determining viral co-receptor usage. No single changes seem to be responsible for tropism, although several clusters of genotypes could determine viral tropism. Several algorithms have been produced to predict HIV co-receptor usage based on the V3 genetic sequence.

However, there is an urgent need for a viral envelope tropism determination assay, which can accurately and with high sensitivity determine the co-receptor usage of a virus strain. Furthermore, because of the development of successful entry inhibitors, assays aimed at evaluating the impact of viral envelope variation on resistance to entry inhibitors and fusion inhibitors will undoubtedly become very important for guiding HIV therapy.

Since patients infected with HIV harbors a diversity of viral subspecies, each with their own co-receptor usage, it is important to analyze the distribution of tropism phenotypes in the entire patient viral population. Furthermore, since methods to predict tropism phenotypes are based on nucleotide and/or amino acid sequences of highly variable regions, it is necessary to determine sequences at clonal level.

So, there definitely exists an unmet high need to have reliable methods in place permitting the characterization of viral tropism in HIV infection in a patient to contribute substantially to our knowledge of the variability and distribution of CCR5 and CXCR4-tropic quasi-species within clinical isolates by means of techniques that are simple and accessible to any analysis laboratory, systems which are so far unavailable.

The present disclosure describes a method and accordingly a tropism test to identify HIV co-receptor usage as a marker for disease progression.

At least two tropism prediction algorithms PSSM (University of Washington, Webpssm) and Geno2-Pheno (G2P), indicated for the tool which is a support vector machine approach (SVM) (Max Plank Institut) are publicly available, both based on the analysis of specific amino acid characteristics of the V3-loop of HIV-1 env. The predictive value however of these algorithms is still limited.

Using clonal V3 env sequences, a comparison was made between the predictions yielded by the PSSM and those obtained by the SVM model. A high concordance was found for R5-tropic isolates between both program models, while X4 predictions were significantly less concordant.

More specifically the instant disclosure describes a method for predicting quantitative phenotype, e.g. gag phenotype, integrase phenotype or tropism, in a patient infected by HIV comprising
 a) using a sample comprising viral genetic material from the patient;
 b) extraction of viral genetic material from said sample followed by single genome sequencing comprising the following steps:
  1. amplification of the viral genetic material of a specific HIV region
  2. analysis of amplicon integrity and pooling of samples
  3. purification of the pooled amplicons
  4. ligation of the pool of amplicons into a vector and transformation of the ligated product into competent cells
  5. analysis of individual transformants obtained
  6. sequencing the resulting single clones to obtain a single clone genotype sequence;
 c) prediction of a specific phenotype, e.g. gag phenotype, integrase phenotype or tropism, using said genotype sequence with a predictive algorithm comprising the following steps:
  1. identifying the genetic pattern in said genotype sequence wherein at least one natural variability, acquired variability, drug selected mutation or mutation pattern is associated with the quantitative phenotypic outcome, e.g. gag phenotype, integrase phenotype or tropism,
  2. searching a genotype/phenotype correlative database for at least one genotype entry with a similar genetic pattern to at least one of the natural variability, acquired variability, drug selected mutation or mutation pattern identified in the genetic sequence in step c1,
  3. obtaining the said at least one genotype entry with a similar genetic pattern with a matched phenotype in the correlative genotype/phenotype database, and,
  4. predicting the HIV phenotype from the database of the at least one genotype entry with a similar genetic pattern;
 d) prediction of the quantitative phenotype, e.g. gag phenotype, integrase phenotype or tropism, based on the information obtained in steps c1 to c4 for every single sequence clone present in a sample of a HIV infected patient.

The method according to the invention may further comprise the following two additional steps after step (c) and before step (d) wherein
 1. clonal sequences without predictable phenotype are analyzed in a single clone biological phenotyping assay and
 2. the information obtained after said analysis is loaded in the correlative genotype-phenotype database used in step (c).

The single clone biological phenotyping assay above-mentioned comprises the following steps:
 1. generation of clonal partial or full-length HIV genome
 2. transfection of mammalian cells with said genome either together with a suitable backbone to obtain recombinant HIV or directly as a full length HIV-1 genome 3. infection of cell lines by said recombinant HIV to determine their biological phenotype wherein the infection process is occurring
4. whereafter the information obtained is loaded in the correlative genotype-phenotype database used in step (c).

Two of the above-mentioned mentioned steps viz. step 2 (transfection) and step 3 (infection) may be performed in a single step.

The amplification of the viral genetic material of a specific HIV region in step (b1) is either performed by RT-PCR or by PCR. The competent cells used in step (b4) are *E. Coli*, *Bacillus* or yeast.

The infection process above mentioned can be monitored either by a marker gene introduced in the full-length HIV genome or by a marker gene introduced in an indicator cell line, or microscopically by cytopathic effect scoring, or by syncitia formation.

In another embodiment of the current invention, HIV sequences obtained and sequenced from samples of patients infected by HIV are loaded into the correlative genotype-phenotype database following the algorithm for prediction of quantitative phenotype, e.g. gag phenotype, integrase phenotype or tropism where after said phenotype or tropism is reported.

With gag phenotype is meant e.g. protease or gag inhibitor resistance, while with integrase phenotype is meant e.g. entry inhibitor resistance.

Samples from a patient used for performing the method are obtained from a biological sample chosen from a blood sample, a biopsy sample, a plasma sample, a saliva sample, a tissue sample, and a bodily fluid or mucous sample.

In addition to the current method and according to the invention, viral load is determined in the sample of a patient infected by HIV.

Part of the invention is the prediction of the quantitative tropism as the quantitative shift in HIV-1 co-receptor usage e.g. from either CCR5 to CXCR4, from CXCR4 to CCR5, or from dual tropic viruses to either CCR5 or CXCR4.

In another embodiment of the instant invention, the prediction of the quantitative gag-phenotype is brought into relation of HIV-1 protease enzymatic activity as a consequence of natural variability or drug-induced/selected variability in the gag open reading frame and/or at the gag-cleavage site.

Alternatively part of the invention is the prediction of the quantitative integrase-phenotype which is brought into relation of HIV-1 integrase enzymatic activity as a consequence of natural variability or drug-induced/selected variability in the integrase open reading frame and/or integrase donor/acceptor sites.

As a final result of the method according to the invention a report is generated wherein said report comprises the predicted phenotype or tropism providing the treating physician with guidance for HIV therapy or treatment.

Part of the invention is also a computer readable medium comprising the predicted phenotype or tropism using any of the methods performed according to the current invention.

To the current invention also belongs the vector pHXB2D-ΔNH$_2$-V4-eGFP having SEQ ID NO: 6 and the use of said vector pHXB2D-ΔNH$_2$-V4-eGFP having SEQ ID NO: 6 in any of the above mentioned methods.

DESCRIPTION OF THE DRAWINGS

Figure 6:
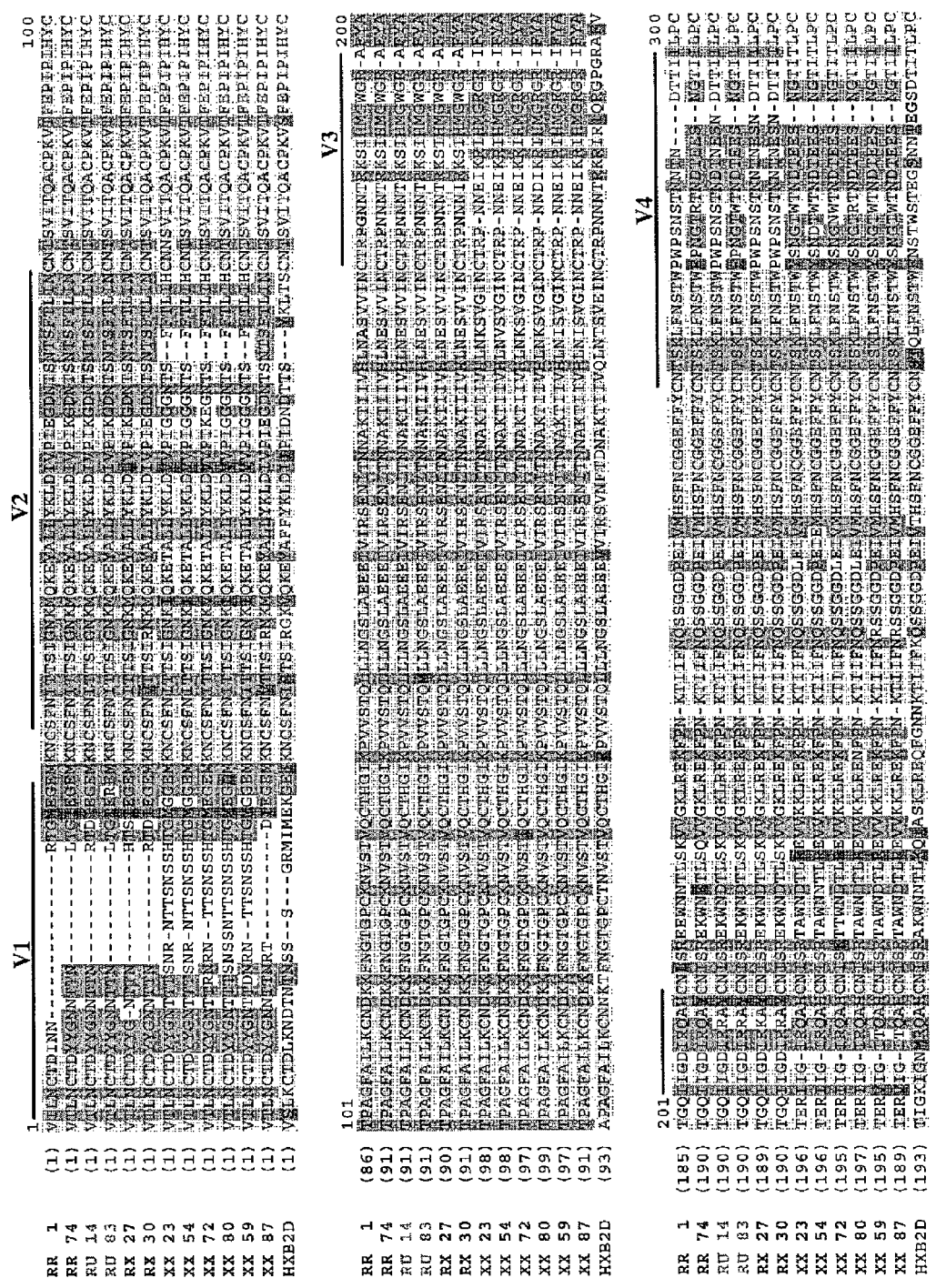

FIG. 6. Nucleotide alignment of the NH$_2$-V4 region of 12 selected clones and HXB2D Conservative base pairs are shown in blue, while identical base pairs are presented in yellow. Env V1, V2, V3 and V4 loops are indicated by red lines.

DETAILED DESCRIPTION

Examples

Example 1

RNA Extraction

Figure 1:
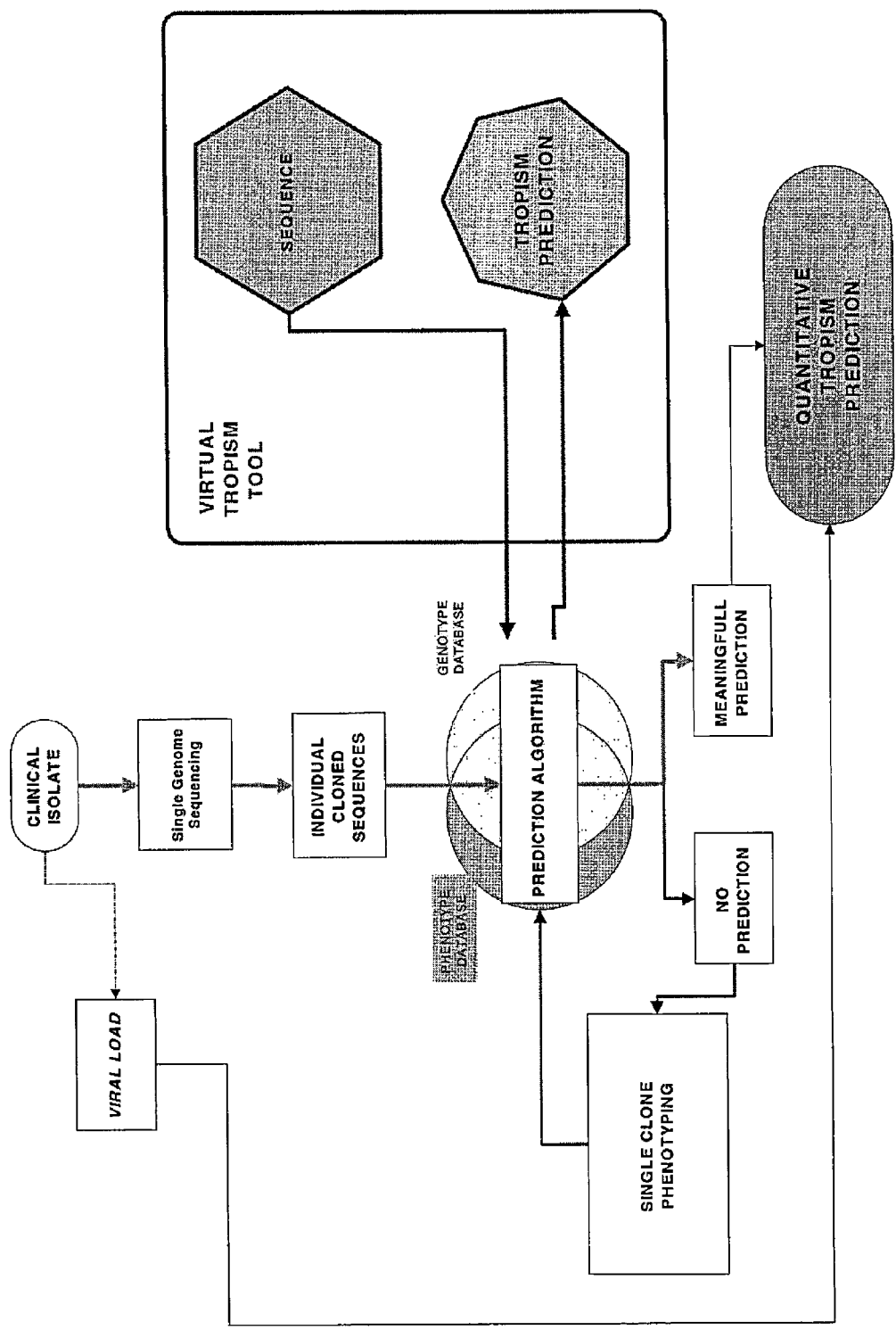
In FIG. 1 a flow-chart shows the method outlined as used in the current invention.
Figure 2:
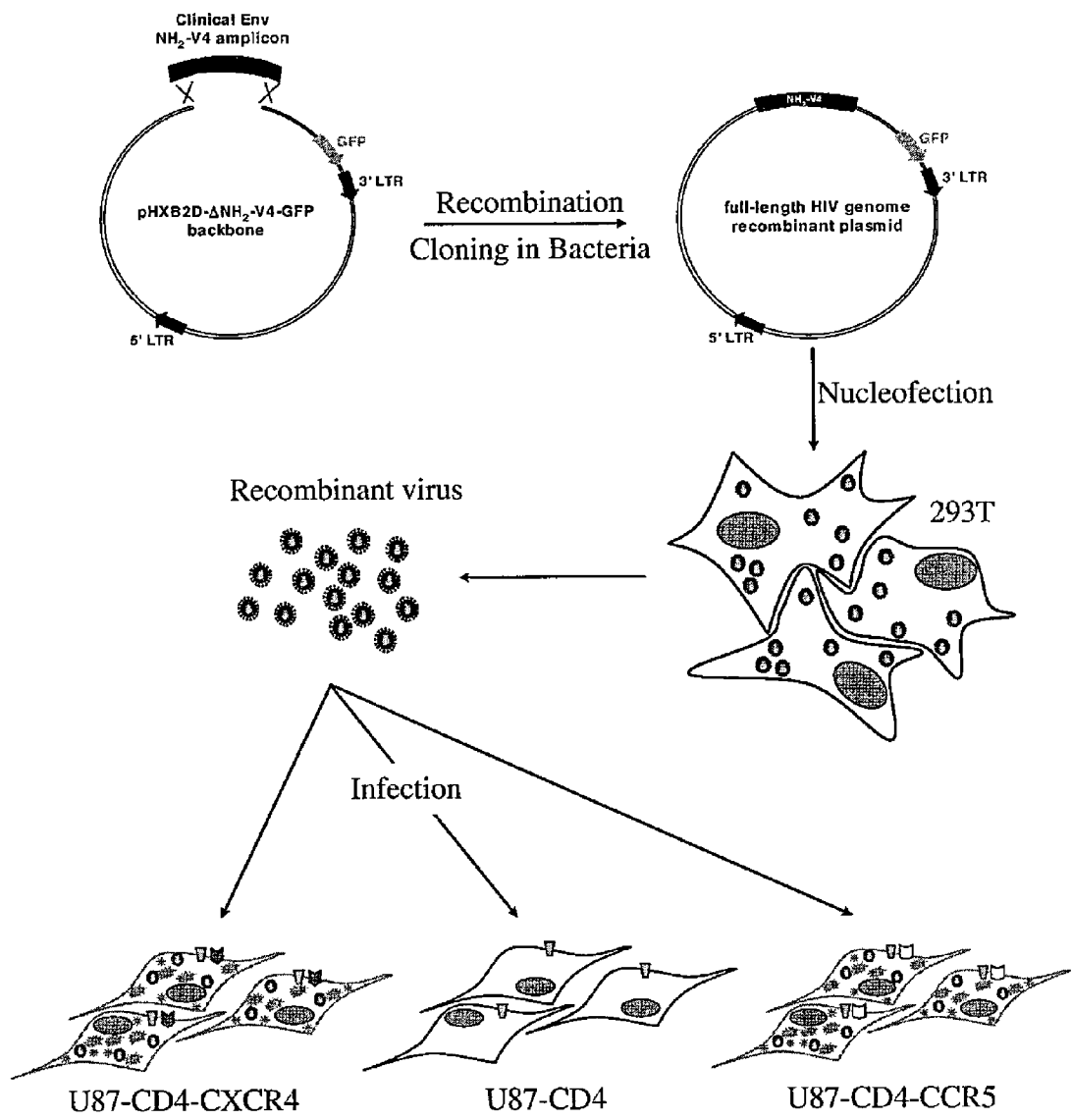
FIG. 2 shows the schematic presentation of recombination clinical env NH$_2$-V4 amplicon into pHXB2D-ΔNH$_2$-V4-eGFP (SEQ ID NO: 6) backbone, cloning into bacteria, nucleofection of full length HIV genome recombinant plasmid in 293 T cells and infection of recombinant virus into U87-CD4 (-CXCR4 or -CCR5) cells.
Figure 3:
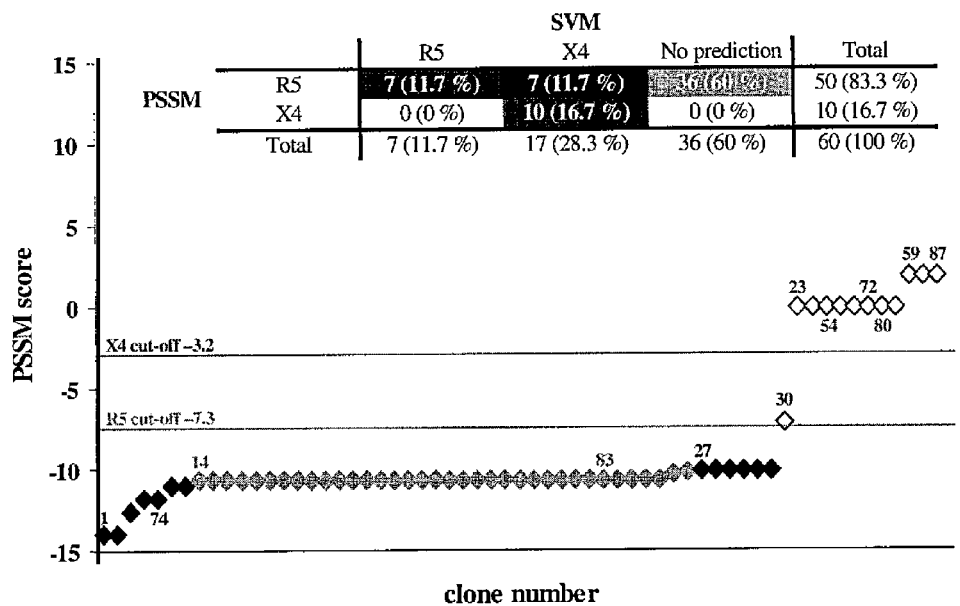
FIG. 3. PSSM scores according to clone number. Clones were subdivided into groups according to their prediction by PSSM and SVM. Clones selected for phenotyping are marked by their corresponding numbers.
Figure 4:
FIG. 4. Sequence logo representing the variability of the V3 loop present in the 60 clones. The overall height of each stack in the logo indicates the sequence conservation at that position, whereas the height of each letter within the stack is proportional to its relative frequency at that position.
Figure 5:
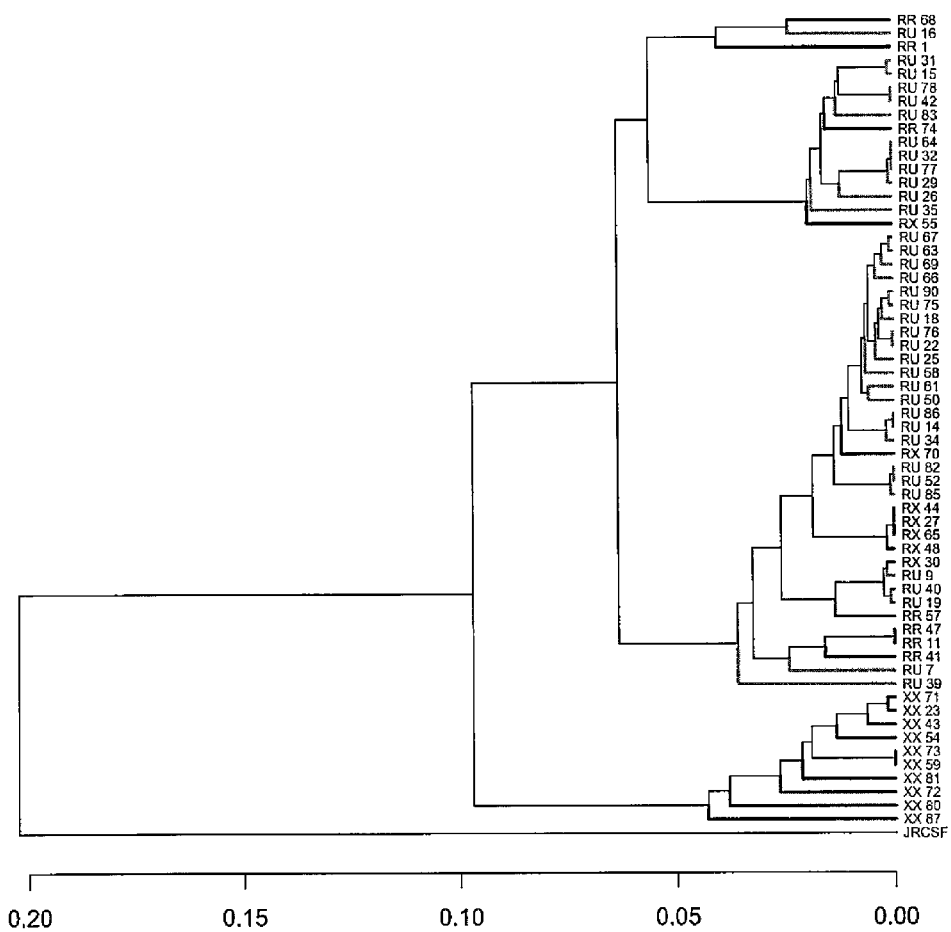
FIG. 5. Phylogenetic tree for the HIV-infected subject under investigation. Branches were colored according to the classification based on the prediction by PSSM and SVM: dark green: predicted R5 by both programs; light green: predicted R5 by PSSM and no prediction by SVM; blue: R5 prediction by PSSM and X4 prediction by SVM; red: X4 prediction by both programs. Bootstrap values of the X4 sequences are shown at the base of its branches. Scale indicates genetic distances based on the nucleotide alignment.

Three clinical plasma samples were randomly selected and were referred to as patient 1, 2 & 3. From a total of 300 µl plasma, total RNA was extracted using the EASYMAG™ RNA extraction platform (Biomérieux, Boxtel, The Netherlands). After elution in 25 µl elution buffer, 5 µl of the eluate was used for viral load measurement using the NucliSens EasyQ® HIV-1 v1.1 system (Biomérieux, Boxtel, The Netherlands). The remainder of the RNA samples was used for amplicon generation.

Amplicon Generation

The remaining 20 µl RNA was mixed with 2× reaction buffer, 0.2 µM primer Env_6210F (CAGAAGACAGTGGCAATGAGAGTGA) (SEQ ID NO: 1), 0.2 µM primer HMA_R3 (ATGGGAGGGGCATACATTGCT) (SEQ ID NO: 2) and 2 units Platinum® Taq High Fidelity from the SuperScript® III One-Step RT-PCR System (Invitrogen, Merelbeke, Belgium) in a total volume of 120 µl. This mixture was divided over eight reactions of 15 µl each and reverse transcription took place at 53° C. for 30 min. Initial denaturation was 94° C. for 2 min and thermal cycling consisted out of 50 cycles of denaturation at 92° C. for 15 s, annealing at 55° C. for 30 s and elongation at 68° C. for 1 min 20 s. Final extension took place at 68° C. for 7 min. The resulting amplicons were pooled, analyzed using the LC90 platform (Caliper, Mountainview, Calif.) and subsequently purified using the QiaQuick® gel purification kit (Qiagen, Hilden, Germany). Final volume of the purified amplicon pools was 30 µl.
TOPO-TA Cloning®
A total of 2 µl of the purified amplicon pools was used for ligation into the pCR®4-TOPO® vector (commercially available) from the TOPO TA Cloning® Kit for Sequencing (Invitrogen, Merelbeke, Belgium) and one aliquot One Shot® TOP10 chemically competent cells (Invitrogen, Merelbeke, Belgium) was transformed with 2 µl of the cloning reaction mixture according to manufacturers instructions.
Colony PCR
Using a sterile tip, a total of 95 colonies (plus one blanc control reaction) was picked (manually or using a robot) per clinical sample to inoculate 50 µl PCR reaction mixture. The latter consisted out of 10×PCR buffer, 25 mM dNTPs, 0.33 µM primer T3 (ATTAACCCTCACTAAAGGGA) (SEQ ID NO: 3), 0.33 µM primer T7 (TAATACGACTCACTATA GGG) (SEQ ID NO: 4) and 0.03 units Expand High Fidelity Enzyme Mix (Roche, Penzberg, Germany). Thermal cycling started with 10 min denaturation at 94° C., 10 cycles of denaturation at 94° C. for 15 s, annealing at 50° C. for 30 s and elongation at 72° C. for 2 min. This was followed by 20 cycles of denaturation at 94° C. for 15 s, annealing at 50° C. for 30 s and elongation at 72° C. for 2 min with an increment of 5 s per cycle. Final extension took place at 72° C. for 7 min. Colony PCR products were purified using the Qiagen 9600 PCR purification platform, eluting in 50 µl (Qiagen, Hilden, Germany).
Cycle Sequencing
From each purified colony PCR product, 1 µl was mixed with 2.5× dilution buffer, 1 µl BigDye® Terminator Mix and 0.2 µM sequencing primer in a total volume of 11.5 µl. Each product was sequenced using primer T3 and T7 in a separate reaction. Thermal cycling consisted out of 25 cycles of denaturation at 96° C. for 10 s, annealing at 50° C. for 5 s and elongation at 60° C. for 4 min. Excess BigDye® was removed using ethanol/sodium acetate precipitation and products were denatured for 2 min at 95° C. and analyzed on the ABI3730 capillary sequencer.
Raw Sequencing Analysis
Electropherograms were retrieved from the ABI3730 capillary sequencer and imported into Seqscape v2 (Applied Biosystems, Foster City, Calif., USA). Sequence ends were trimmed based on quality values and the length of the JR-CSF reference sequence; the latter spanned the region between the amplification primers. Certain clones were removed from the analysis when the generated sequence:
- did not span the entire region of interest between the amplification primer sequences
- contained a STOP codon Tropism Prediction
1. V3-Loop Amino Acid Sequence Extraction
Because the PSSM prediction algorithm requires amino acid sequences, correct translation of the V3-region out of the nucleotide sequences spanning the entire range from the amino terminal part of Env up to the V4-loop was performed. By performing a BLAST search of the translated nucleotide sequences (in all 6 frames) vs. a small database containing the HXB2 V3-loop amino acid sequence, the region with the highest match with V3 could be demarcated. Subsequently these regions were extracted and translated.
2. PSSM Tropism Prediction
The position specific scoring matrix (PSSM) prediction was generated by uploading the V3-loop amino acid sequences (PSSM algorithm, University of Washington, Webpssm) according to Jensen, M. A., F. S. Li, A. B. van 't Wout, D. C. Nickle, D. Shriner, H. X. He, S. McLaughlin, R. Shankarappa, J. B. Margolick, and J. I. Mullins. 2003. Improved coreceptor usage prediction and genotypic monitoring of R5-to-X4 transition by motif analysis of human immunodeficiency virus type 1 env V3 loop sequences. J Virol 77:13376-88.
3. Support Vector Machine (SVM) Algoritm as Available in the Geno2-Pheno Tropism Prediction Tool
Since the geno2-pheno co receptor prediction tool (indicated as SVM) does not allow batch submitting of nucleotide sequences, a Perl script was written that automates submission of all the sequences and an HTML output (SVM) was then parsed with another perl script to yield geno2-pheno tropism predictions per patient.
4. Comparison of SVM and PSSM Tropism Predictions
A SAS script puts all predictions into 1 dataset and makes contingency tables for each patient.
Results.
Three clinical isolates were randomly selected. From each isolate, viral RNA was reverse transcribed, amplified several times, and the obtained amplicons pooled, purified and cloned in bacterial cells. More than 50 randomly selected clones were sequenced and submitted to the two prediction programs. The result of this analysis is shown in table 1.

TABLE 1

Tropism prediction on individual V3 clones obtained from clinical isolates

|  | PSSM | G2P CCR5 | CXCR4 | DUAL | NONE | TOTAL |
|---|---|---|---|---|---|---|
| PATIENT 1 | R5 |  |  |  | 55 | 55 |
|  | X4 |  | 1 |  |  |  |
| PATIENT 2 | R5 | 7 | 7 |  | 36 | 50 |
|  | X4 |  | 10 |  |  | 10 |
| PATIENT 3 | R5 | 2 | 19 | 1 | 27 | 49 |
|  | X4 |  | 5 |  |  | 5 |

G2P: prediction tool using a SVM approach (Max Plank Institut);
PSSM: prediction tool (University of Washington, Webpssm).
DUAL: V3 sequences predicted to infect both CCR5 and CXCR4 expressing cells.
NONE: no prediction available in SVM at the standard settings.

For every patient tested in this study, there is a significant amount of clonal sequences that resulted in no prediction in the SVM algorithm, while a prediction was obtained in the PSSM method. Further improvements of the prediction tools that are based on larger relational databases are needed to fine-tune these predictions. A single clone phenotyping assay is instrumental to build such database.

Example 2

Single Clone Phenotyping Assay

Patient-derived clonal sequences constituting complete gp160 or part of gp160 were introduced via the BD In Fusion system into hXB2D-eGFP backbone in which complete gp160 or part of it, respectively, was deleted (SEQ ID NO: 5). HXB2D-eGFP is a vector containing GFP instead of nef (Chen et al (1997), J Virol 71: 5495-5504). Instead of eGFP as marker other well known markers such as luciferase or other commercially available fluorescent proteins, can be used in the current assay. For every patient-derived full-length recombinant HIV-eGFP clone generated in this way, DNA was prepared and checked by restriction analysis. One µg of positive clones was transfected to 293T cells using the Amaxa nucleofection technique. Supernatant virus cultures were harvested 24-48 h after transfection and used to infect U87 cells (U87 parental, U87-CD4, U87-CD4-CXCR4 and U87-CD4-

CCR5 cells). Co receptor usage was determined 24-96 h after infection by fluorescence microscopy. Alternatively, supernatant virus cultures were used to infect U87 containing CXCR4-CCR5 chimeric receptors (Karlsson et al (2003) AIDS 17: 2561-2569). In this way, predictions concerning the potency of a CCR5-using virus to shift to a CXCR4-tropic virus are performed.

Example 3

Clonal Phenotypic Confirmation of Genotypic V3-Loop Tropism Prediction on a Treatment-Naïve HIV-1 Infected Subject Sample RNA Extraction and VIRCOTYPE™

From a total of 300 μl plasma obtained from a randomly selected HIV-1-infected subject, RNA was extracted using the EASYMAG™ RNA extraction platform (Biomérieux, Boxtel, The Netherlands). Viral load was determined by NucliSens EasyQ® HIV-1 v1.1 system (Biomérieux; output in IU/ml). A VIRCOTYPE™ resistance analysis was generated.

Amplification

RNA was reverse transcribed and amplified using SuperScript™ III One-Step RT-PCR System with Platinum® Taq High Fidelity (Invitrogen, Merelbeke, Belgium) in 7-fold. The forward primer was situated before the start codon of Env, the reverse primer in the Env C4 region.

The PCR fragment was called $NH_2$-V4 amplicon.

Clonal Sequencing

After pooling, the amplicon was cloned into pCR4-TOPO® vector (Invitrogen). After transformation into competent TOP10 *E. coli* cells, individual clones were picked and inserts amplified by colony PCR using forward and reverse plasmid primers. After purification, colony PCR products were sequenced using the BigDye® Terminator cycle sequencing kit (Applied Biosystems, Foster City, Calif., USA), and run on an ABI 3730 XL automated sequencer. Sequence editing and contig assembly were performed using SeqScape v2.5 (Applied Biosystems).

Data Analysis

Alignments were constructed using ClustalW (European Bioinformatics Institute), and used as input for creating a sequence logo in the WebLogo sequence logo generator program (University of California, Berkeley). Viral tropism was predicted based on the V3 loop sequence by the PSSM algorithm (University of Washington, Webpssm) and SVM (Max Plank Institut) using the standard settings as provided with the programs on the websites. Phylogenetic analysis was based on a nucleotide alignment of the full $NH_2$-V4 sequence (~1260 bp). Distances were calculated (DNADIST), trees were constructed (NEIGHBOR), and finally, a consensus tree was built (CONSENSE). N-linked glycosylation of the V3-loop was assessed by the EMBOSS program patmatdb (Institut Pasteur, France). $NH_2$-V4 sequence-based clading was performed by alignment of all clonal sequences with the same region of 66 HIV-1 clade reference strains downloaded from the Los Alamos HIV electronic database (Los Alamos National Library). Similarity tables were retrieved and the reference strains showing the highest percentage of identity with all clones were recorded.

Clonal Phenotyping

Clonal $NH_2$-V4 amplicons were recombined into pHXB2D-Δ$NH_2$-V4-eGFP an hXB2D-based eGFP-containing $NH_2$-V4-deleted backbone (SEQ ID NO: 6), using In-Fusion® CF Dry-Down Cloning Kit (BD Biosciences, Erembodegem, Belgium). Instead of eGFP as marker other well known markers such as luciferase or other commercially available fluorescent proteins, can be used in the current assay. After transformation into MAX Efficiency Stbl cells (Invitrogen), DNA was prepared using QiaPrep® Spin Miniprep Kit (Qiagen, Hilden, Germany). After transfection of the recombinant plasmids into 293T cells using the Amaxa nucleofection technique, produced viruses were used to infect U87-CD4, U87-CD4-CXCR4 and U87-CD4-CCR5 cells. (FIG. 2). After 120 h incubation at 37° C., infection was visualized by fluorescence microscopy. Recombinant plasmids and virus stocks were sequenced using the BigDye® Terminator cycle sequencing kit (Applied Biosystems), and run on an ABI 3730 XL automated sequencer. Sequence editing and contig assembly were performed using SeqScape v2.5 (Applied Biosystems).

Results

Clonal Genotypic V3-Loop Tropism Prediction

One HIV-1-infected subject was randomly selected for clonal genotypic and phenotypic tropism analysis. VIRCOTYPE™ analysis showed that the selected HIV-1 strain was susceptible to all FDA-approved proteases and RT inhibitors. Furthermore, the plasma sample contained a viral load of 5.48 log IU/ml indicating that the subject was treatment-naïve. Both GPRT-based (VIRCOTYPE™) and Env $NH_2$-V4-sequence-based clading showed that the selected strain was clade B.

After RNA extraction, the $NH_2$-V4 region was amplified in 7-fold in a single round RT-PCR reaction. After pooling and cloning the $NH_2$-V4 amplicon into the pCR4-TOPO vector, a total of 95 colonies were picked for sequencing. Two clones contained no $NH_2$-V4 insert and 4 clones contained a premature stop codon.

Out of the 89 remaining clones, 60 were selected for tropism prediction by algorithms PSSM (Position Specific Scoring Matrix) and SVM (Support Vector Machine). Four different categories were characterized: RR, XX, RX, and RU with R=R5-tropic, X=X4-tropic, U=unpredictable whereby the first letter in each duplet represents the prediction by PSSM and the second by SVM. Between the 2 algorithms, 11.7% concordant R5 and 16.7% concordant X4 predictions were observed. Almost 12% of the clones showed a discordant prediction (R5 by PSSM and X4 by SVM) and 60% of the clones yielded no prediction by SVM. The PSSM plot (FIG. 3) and sequence logo (FIG. 4) demonstrated a great variability in the selected HIV-1 strain. Further, it was observed that the PSSM scores gradually increased from 1) clones that were predicted R5 by both programs (RR group) to 2) clones with R5 by PSSM versus no prediction by SVM (RU group) to 3) clones with discordant results (R5 by PSSM and X4 by SVM, RX group) to 4) concordant X4 clones (XX group). Finally, it could be observed that only one clone (from the RX group) was situated in the intermediate zone between the cut-off for R5 prediction (−7.3) and the cut-off for X4 prediction (−3.2).

To demonstrate the relatedness among the sequences, phylogenetic analysis was performed for the complete $NH_2$-V4 nucleotide region (FIG. 5). Besides the great variability, it was clear that X4 clones cluster together and the genetic distance between X4 clusters and R5 clusters is relatively short. X4 clustering was significant as assessed by bootstrapping.

All clones were screened for the presence of the N-linked glycosylation motif N {P} S/T {P}, which might be involved in the interaction of R5 gp120 with CCR5, while it might preclude CXCR4 usage. In total, 11 clones lacked the glycosylation motif: 10 clones from the XX group and 1 clone from the RX group, which was located in the intermediate zone of PSSM scoring (clone 30).

Clonal Phenotypic Tropism Determination Twelve clones were selected for phenotypic tropism determination: clone 1 and 74 (RR group), clone 14 and 83 (RU group), clone 27 and 30 (RX group) and clone 23, 54, 59, 72, 80 and 87 (XX group). An NH$_2$-V4 nucleotide alignment including some characteristics of the selected clones was performed and shown in FIG. 6.

Each clonal NH$_2$-V4 region was recombined into pHXB2D-ΔNH$_2$-V4-eGFP (SEQ ID NO: 6) backbone vector to obtain HIV full genome plasmids, carrying eGFP in nef. After transfection into 293T cells, replication-competent recombinant virus stocks were obtained. Sequencing the NH$_2$-V4 region, including the recombination sites, of both recombinant plasmids and recombinant virus stocks revealed no mismatches when compared to the original clonal sequences obtained in the clonal genotyping experiments.

Figure 7:
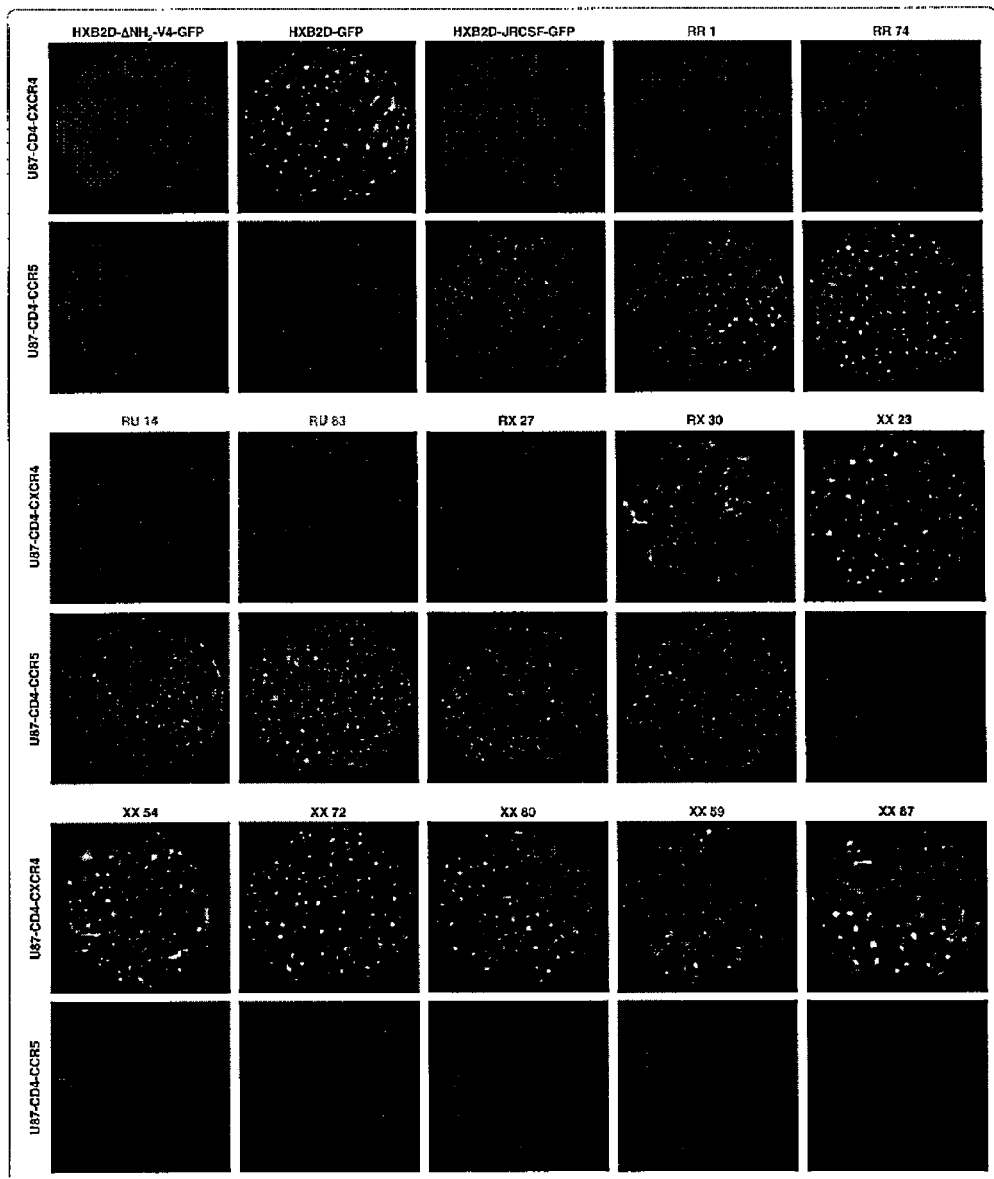
FIG. 7. Fluorescent microscopic images of U87-CD4-CXCR4 and U87-CD4-CCR5 infected with 12 selected clones and positive (HXB2D-eGFP and HXB2D-JRCSF-eGFP) and negative controls (HXB2D-ΔNH$_2$-V4-eGFP) (SEQ ID NO: 6).

Recombinant virus stocks were tested phenotypically by infection of U87-CD4, U87-CD4-CXCR4 and U87-CD4-CCR5 cells (FIG. 7). Clones selected from the RR group and the RU group were R5-tropic only, while clones selected from the XX group showed CXCR4 usage only. One clone selected from the RX group showed CCR5 usage (clone 27), while another clone from this group was phenotyped as being dual-tropic (clone 30). Interestingly, the latter clone showed an intermediate PSSM score of −7.11.

Clonal genotypic and phenotypic tropism analysis on a treatment-naïve HIV-1-infected subject revealed the presence of both R5-, dual-, and X4-tropic virus strains. Tropism algorithms were accurate for isolates with clear affinity for their co-receptor (RR and XX group, possibly also the RU group), and need refinement for isolates showing discordant predictions (RX and possibly the RU group).

The above demonstrates that this platform allows quantitative (NH$_2$-V4 clonal sequencing and NH$_2$-V4 clonal phenotyping) tropism testing with accurate reproduction of the viral quasi-species present in the original patient's sample. In addition NH$_2$-V4 population phenotyping was performed on 40 different HIV-1 samples and a good correlation was observed between V3 population sequencing and said NH$_2$-V4 population phenotyping.

The invention claimed is:

1. A method for predicting quantitative tropism, quantitative tropism being the quantitative shift in HIV-1 co-receptor usage from CCR5 to CXCR4, from CXCR4 to CCR5, or from dual trophic virus to either CCR5 or CXCR4, in a patient infected by HIV comprising:

a) using a sample comprising viral genetic material from the patient;

b) extraction of viral genetic material from said sample followed by single genome sequencing comprising the following steps:

1. amplification of the viral genetic material of a specific HIV region;
2. analysis of amplicon integrity and pooling of samples;
3. purification of the pooled amplicons;
4. ligation of the pool of amplicons into a vector and transformation of the ligated product into competent cells;
5. analysis of individual transformants obtained; and
6. sequencing the resulting single clones to obtain a single clone genotype sequence;

c) prediction of the specific tropism using said genotype sequence with a predictive algorithm comprising the following steps:

1. identifying the genetic pattern in said genotype sequence wherein at least one natural variability, acquired variability, drug selected mutation or mutation pattern is associated with the quantitative tropism,
2. searching a genotype/phenotype correlative database for at least one genotype entry with a similar genetic pattern to at least one of the natural variability, acquired variability, drug selected mutation or mutation pattern identified in the genetic sequence in step c)1,
3. obtaining the said at least one genotype entry with a similar genetic pattern with a matched phenotype in the correlative genotype/phenotype database, and
4. predicting the HIV tropism from the database of the at least one genotype entry with a similar genetic pattern;

d) analysis of clonal sequences without predictable phenotype in a single clone biological phenotyping assay, wherein the information obtained after said analysis is loaded into the correlative genotype-phenotype database used in step c), wherein the single clone biological phenotyping assay comprises the following steps:
1. generation of clonal partial or full-length HIV genome by using vector pHXB2D-≠NH2-V4-eGFP having SEQ ID NO: 6;
2. transfection of mammalian cells with said genome either together with a suitable backbone to obtain recombinant HIV or directly as a full length HIV-1 genome; and
3. infection of cell lines by said recombinant HIV to determine their biological phenotype wherein the infection process is occurring;

e) prediction of the quantitative tropism based on the information obtained in steps c)1 to c)4 for every single sequence clone present in a sample of a HIV infected patient.

2. The method according to claim 1 wherein step d)2 (transfection) and step d)3 (infection) of the single clone biological phenotyping assay are performed in a single step.

3. The method according to claim 1 wherein the amplification of the viral genetic material of a specific HIV region in step b)1 is either performed by reverse transcription polymerase chain reaction (RT-PCR) or by polymerase chain reaction (PCR).

4. The method according to claim 1 wherein the competent cells used in step b)4 are *E. Coli*, yeast or *Bacillus*.

5. The method according to claim 1, step d) wherein the infection process is monitored either by a marker gene introduced in the full-length HIV genome or by a marker gene introduced in an indicator cell line, or microscopically by cytopathic effect scoring or by syncitia formation.

6. The method according to claim 1 whereby HIV sequences obtained and sequenced from samples of patients infected by HIV are loaded into the correlative genotype-phenotype database following the algorithm for prediction of quantitative tropism where after said tropism is reported.

7. The method according to claim 1 wherein said sample from the patient is obtained from a biological sample chosen from a blood sample, a biopsy sample, a plasma sample, a saliva sample, a tissue sample, and a bodily fluid or mucous sample.

8. The method according to claim 1 where in addition viral load is determined in the sample of a patient infected by HIV.

9. The method according to claim 1 wherein the prediction of the quantitative tropism is the quantitative shift in HIV-1 co-receptor usage from either CCR5 to CXCR4 or from CXCR4 to CCR5.

10. A method of generating a report wherein said report comprises the predicted tropism using the method of claim 1.

11. A pHXB2D-ΔNH2-V4-eGFP vector having SEQ ID NO: 6.

* * * * *